(12) United States Patent
Chiou et al.

(10) Patent No.: US 9,670,243 B2
(45) Date of Patent: Jun. 6, 2017

(54) COMPOSITIONS AND METHODS FOR SEQUENCING NUCLEIC ACIDS

(75) Inventors: Chung-Fan Chiou, Hsinchu (TW); Chao-Chi Pan, Hsinchu (TW); Jenn-Yeh Fann, Hsinchu County (TW); Shang-Chia Chang, Zhubei (TW); Tsu-Ju Fu, Hukou Township, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 1739 days.

(21) Appl. No.: 13/117,565

(22) Filed: May 27, 2011

(65) Prior Publication Data

US 2011/0300534 A1     Dec. 8, 2011

Related U.S. Application Data

(60) Provisional application No. 61/350,693, filed on Jun. 2, 2010.

(51) Int. Cl.
| | |
|---|---|
| *C12Q 1/68* | (2006.01) |
| *C12P 19/34* | (2006.01) |
| *C07H 21/04* | (2006.01) |
| *C07H 21/02* | (2006.01) |
| *C07H 19/04* | (2006.01) |

(52) U.S. Cl.
CPC ........... *C07H 21/04* (2013.01); *C12Q 1/6869* (2013.01); *C12Q 2525/117* (2013.01); *C12Q 2525/119* (2013.01)

(58) Field of Classification Search
CPC ............ C12Q 1/6869; C12Q 2525/117; C12Q 2525/119; C07H 21/04

USPC .......... 435/6.1, 91, 91.1; 536/4.1, 23.1, 26.6
See application file for complete search history.

(56) References Cited

U.S. PATENT DOCUMENTS

| | | | |
|---|---|---|---|
| 5,302,509 | A | 4/1994 | Cheeseman |
| 5,391,480 | A | 2/1995 | Davis et al. |
| 5,405,747 | A | 4/1995 | Jett et al. |
| 5,460,975 | A | 10/1995 | Freitag et al. |

(Continued)

FOREIGN PATENT DOCUMENTS

| | | |
|---|---|---|
| CN | 101168773 A | 4/2008 |
| CN | 101384729 A | 3/2009 |

(Continued)

OTHER PUBLICATIONS

Abramova, T.V. et al., "Design and synthesis of dinucleotide 5'-triphosphates" *Bioorg. Med. Chem.*, 16:9127-32 (2008).

(Continued)

*Primary Examiner* — Jezia Riley
(74) *Attorney, Agent, or Firm* — Finnegan, Henderson, Farabow, Garrett and Dunner LLP

(57) ABSTRACT

Embodiments relate to methods of sequencing nucleic acids. Embodiments encompass the use of nucleotide analogs and a nucleic acid polymerase enzyme or enzyme complex comprising proofreading activity. The nucleotide analogs may become incorporated into a replicating strand and induce the proofreading activity of the polymerizing enzyme, thereby prolonging the duration of a signal associated with nucleotide incorporation, resulting in more observable sequencing events and increasing the accuracy of nucleic acid sequencing.

28 Claims, 5 Drawing Sheets

(56) References Cited

U.S. PATENT DOCUMENTS

| | | |
|---|---|---|
| 5,674,743 A | 10/1997 | Ulmer |
| 5,717,602 A | 2/1998 | Kenning |
| 5,750,341 A | 5/1998 | Macevicz |
| 5,795,782 A | 8/1998 | Church et al. |
| 6,013,434 A | 1/2000 | Tregear et al. |
| 6,123,819 A | 9/2000 | Peeters |
| 6,153,737 A | 11/2000 | Manoharan et al. |
| 6,197,513 B1 | 3/2001 | Coull et al. |
| 6,210,973 B1 | 4/2001 | Pettit |
| 6,232,075 B1 | 5/2001 | Williams |
| 6,255,083 B1 | 7/2001 | Williams |
| 6,287,821 B1* | 9/2001 | Shi et al. ............ 435/91.2 |
| 6,306,607 B2 | 10/2001 | Williams |
| 6,362,002 B1 | 3/2002 | Denison et al. |
| 6,413,792 B1 | 7/2002 | Sauer et al. |
| 6,762,048 B2 | 7/2004 | Williams |
| 6,917,726 B2 | 7/2005 | Levene et al. |
| 6,946,249 B2 | 9/2005 | Head et al. |
| 7,013,054 B2 | 3/2006 | Levene et al. |
| 7,033,764 B2 | 4/2006 | Korlach et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,060,440 B1 | 6/2006 | Kless |
| 7,081,526 B2 | 7/2006 | Marciacq et al. |
| 7,170,050 B2 | 1/2007 | Turner et al. |
| 7,181,122 B1 | 2/2007 | Levene et al. |
| 7,229,799 B2 | 6/2007 | Williams |
| 7,282,337 B1 | 10/2007 | Harris |
| 7,292,742 B2 | 11/2007 | Levene et al. |
| 7,302,146 B2 | 11/2007 | Turner et al. |
| 7,315,019 B2 | 1/2008 | Turner et al. |
| 7,316,930 B1 | 1/2008 | Montalbo |
| 7,329,492 B2 | 2/2008 | Hardin et al. |
| 7,361,466 B2 | 4/2008 | Korlach et al. |
| 7,416,844 B2 | 8/2008 | Korlach et al. |
| 7,485,424 B2 | 2/2009 | Korlach et al. |
| 7,486,865 B2 | 2/2009 | Foquet et al. |
| 7,666,645 B2 | 2/2010 | Wang |
| 7,767,441 B2 | 8/2010 | Chiou et al. |
| 7,805,081 B2 | 9/2010 | Lundquist et al. |
| 7,943,305 B2 | 5/2011 | Korlach et al. |
| 7,943,307 B2 | 5/2011 | Korlach et al. |
| 8,603,741 B2 | 12/2013 | Emig et al. |
| 2002/0090630 A1 | 7/2002 | Hazama |
| 2003/0064366 A1 | 4/2003 | Hardin et al. |
| 2003/0087242 A1 | 5/2003 | Mirkin et al. |
| 2003/0092005 A1 | 5/2003 | Levene et al. |
| 2003/0143724 A1 | 7/2003 | Cerrina et al. |
| 2004/0038331 A1 | 2/2004 | Reddy et al. |
| 2004/0152119 A1 | 8/2004 | Sood et al. |
| 2005/0100932 A1* | 5/2005 | Lapidus et al. ............ 435/6 |
| 2005/0208557 A1 | 9/2005 | Korlach et al. |
| 2005/0266424 A1 | 12/2005 | Hardin et al. |
| 2005/0275839 A1 | 12/2005 | Robinson et al. |
| 2006/0057606 A1 | 3/2006 | Korlach et al. |
| 2006/0068506 A1 | 3/2006 | Uyeda et al. |
| 2006/0134666 A1 | 6/2006 | Korlach et al. |
| 2006/0160113 A1 | 7/2006 | Korlach et al. |
| 2007/0026447 A1 | 2/2007 | Korlach et al. |
| 2007/0141598 A1 | 6/2007 | Turner et al. |
| 2007/0172858 A1 | 7/2007 | Hardin et al. |
| 2007/0172861 A1 | 7/2007 | Hardin et al. |
| 2007/0172862 A1 | 7/2007 | Hardin et al. |
| 2007/0172863 A1 | 7/2007 | Hardin et al. |
| 2007/0172864 A1 | 7/2007 | Gao et al. |
| 2007/0172865 A1 | 7/2007 | Hardin et al. |
| 2007/0172866 A1 | 7/2007 | Hardin et al. |
| 2007/0172867 A1 | 7/2007 | Hardin et al. |
| 2007/0172868 A1 | 7/2007 | Hardin et al. |
| 2007/0184475 A1 | 8/2007 | Hardin et al. |
| 2007/0275395 A1 | 11/2007 | Hardin et al. |
| 2007/0292867 A1 | 12/2007 | Hardin et al. |
| 2008/0050747 A1 | 2/2008 | Korlach et al. |
| 2008/0108082 A1 | 5/2008 | Rank et al. |
| 2008/0176769 A1 | 7/2008 | Rank et al. |
| 2008/0199932 A1 | 8/2008 | Hanzel et al. |
| 2008/0227654 A1 | 9/2008 | Korlach et al. |
| 2008/0241833 A1 | 10/2008 | Williams |
| 2009/0082212 A1 | 3/2009 | Williams |
| 2009/0087850 A1 | 4/2009 | Eid et al. |
| 2009/0137007 A1 | 5/2009 | Korlach et al. |
| 2009/0146076 A1 | 6/2009 | Chiou et al. |
| 2009/0170074 A1 | 7/2009 | Williams |
| 2009/0263797 A1 | 10/2009 | Zon |
| 2009/0275036 A1 | 11/2009 | Hardin et al. |
| 2009/0286245 A1 | 11/2009 | Bjornson et al. |
| 2009/0305278 A1 | 12/2009 | Hardin et al. |
| 2010/0009872 A1 | 1/2010 | Eid et al. |
| 2010/0035268 A1 | 2/2010 | Beechem et al. |
| 2010/0075328 A1 | 3/2010 | Bjornson et al. |
| 2010/0093068 A1 | 4/2010 | Williams |
| 2010/0121582 A1 | 5/2010 | Pan et al. |
| 2010/0255463 A1 | 10/2010 | Harsin et al. |
| 2010/0255487 A1 | 10/2010 | Beechem et al. |
| 2010/0256918 A1 | 10/2010 | Chen et al. |
| 2010/0304358 A1 | 12/2010 | Nie et al. |
| 2010/0304367 A1 | 12/2010 | Hardin et al. |
| 2010/0317005 A1 | 12/2010 | Hardin et al. |
| 2011/0014604 A1 | 1/2011 | Hardin et al. |
| 2011/0014612 A1 | 1/2011 | Hendricks et al. |
| 2011/0021383 A1 | 1/2011 | Hardin et al. |
| 2011/0059436 A1 | 3/2011 | Hardin et al. |
| 2011/0111401 A1 | 5/2011 | Korlach et al. |
| 2011/0223590 A1 | 9/2011 | Chiou et al. |
| 2011/0300534 A1 | 12/2011 | Chiou et al. |
| 2011/0306039 A1 | 12/2011 | Chiou et al. |
| 2011/0306143 A1 | 12/2011 | Chiou et al. |
| 2014/0127680 A1* | 5/2014 | Emig ............ C12Q 1/6869 435/6.1 |
| 2016/0010150 A1* | 1/2016 | Emig ............ C07H 19/10 506/2 |

FOREIGN PATENT DOCUMENTS

| | | |
|---|---|---|
| CN | 101654712 A | 2/2010 |
| EP | 1 102 782 B1 | 3/2006 |
| JP | 2004-523243 A | 8/2004 |
| JP | 2007-531527 A | 11/2007 |
| JP | 2009-537148 A | 10/2009 |
| WO | WO 89/03432 A1 | 4/1989 |
| WO | WO 00/36152 A1 | 6/2000 |
| WO | WO 00/36151 A9 | 8/2001 |
| WO | WO 01/92501 A1 | 12/2001 |
| WO | WO 02/04680 A2 | 1/2002 |
| WO | WO 00/70073 A9 | 4/2002 |
| WO | WO 02/072892 | 9/2002 |
| WO | WO 02/072892 A1 | 9/2002 |
| WO | WO-03/003015 | 9/2003 |
| WO | WO 2004/011605 A2 | 2/2004 |
| WO | WO 2005/019419 A2 | 3/2005 |
| WO | WO 2005/080605 A2 | 9/2005 |
| WO | WO 2005/098042 A2 | 10/2005 |
| WO | WO 2007/119067 A1 | 10/2007 |
| WO | WO 2008/016906 A2 | 2/2008 |
| WO | WO 2009/017678 A2 | 2/2009 |
| WO | WO 2009/145818 A1 | 3/2009 |
| WO | WO 2009/054922 A | 4/2009 |
| WO | WO 2009/056065 A1 | 5/2009 |

OTHER PUBLICATIONS

Notification of Reasons for Refusal issued in Japanese Patent Application No. 2013-512746; Dispatch Date: Jun. 10, 2014, with English translation.

Cheng "High-Speed DNA-Sequence Analysis" *Prog. Biochem. Biophys.* 22:223-227 (1995) (English abstract on p. 227).

Clarke et al. "Continuous base identification for single-molecule nanopore DNA sequencing" *Nature Nanotechnol.* 4:265-270 (2009).

(56) References Cited

OTHER PUBLICATIONS

Dapprich et al. "DNA Attachment to Optically Trapped Beads in Microstructures Monitored by Bead Displacement" *Bioimaging* 6:25-32 (1998).
Dörre et al. "Techniques for Single Molecule Sequencing" *Bioimaging* 5:139-152 (1997).
Eid et al. "Real-Time DNA Sequencing from Single Polymerase Molecules" *Science* 323(5910):133-138 (2009).
Extended European Search Report issued by the European Patent Office, dated Aug. 12, 2011, in European Patent Application No. 10750363.3 (17 pages).
Extended European Search Report issued by the European Patent Office, dated Aug. 16, 2011, in European Patent Application No. 10196884.0 (10 pages).
Fidalgo Da Silva and Reha-Krantz "DNA polymerase proofreading: active site switching catalyzed by the bacteriophage T4 DNA polymerase" *Nucl. Acids Res.* 35(16):5452-5463 (2007).
Goodwin et al. "Application of Single Molecule Detection to DNA Sequencing" *Nucleos. Nucleot.* 16:543-550 (1997).
Harris et al. "Single-Molecule DNA Sequencing of a Viral Genome" *Science* 320:106-109 (2008).
Howorka et al. "Sequence-specific detection of individual DNA strands using engineered nanopores" *Nat. Biotechnol.* 19:636-639 (2001).
Hyman "A New Method of Sequencing DNA" *Anal. Biochem.* 174:423-436 (1988).
Kamtekar et al. "Insights into Strand Displacement and Processivity from the Crystal Structure of the Protein-Primed DNA Polymerase of Bacteriophage ɸ 29" *Mol. Cell.* 16:609-618 (2004).
Kim et al. "Crystal structure of *Thermus aquaticus* DNA polymerase" *Nature* 376:612-616 (1995).
Korlach et al. "Selective aluminum passivation for targeted immobilization of single DNA polymerase molecules in zero-mode waveguide nanostructures" *PNAS USA* 105(4):1176-1181 (2008).
Levene et al. "Zero-Mode Waveguides for Single-Molecule Analysis at High Concentrations" *Science* 299:682-686 (2003).
Medintz et al. "Quantum dot bioconjugates for imaging, labelling and sensing" *Nat. Mater.* 4:435-446 (2005).
McGuire et al. "The Future of Personal Genomics" *Science* 317:1687 (2007).
Metzker "Sequencing technologies—the next generation" *Nat. Rev. Genet.* 11:31-46 (2010).
Moerner et al. "Methods of single-molecule fluorescence spectroscopy and microscopy" *Review of Scientific Instruments* 74(8):3597-3619 (2003).
Reddy et al. "Processive Proofreading Is Intrinsic to T4 DNA Polymerase" *J. Biol. Chem.* 267(20):14157-14166 (1992).
Reha-Krantz "Regulation of DNA Polymerase Exonucleolytic Proofreading Activity: Studies of Bacteriophage T4 'Antimutator' DNA Polymerases" *Genetics* 148:1551-1557 (1998).
Ronaghi et al. "A Sequencing Method Based on Real-Time Pyrophosphate" *Science* 281:363-365 (1998).
Sauer et al. "Detection and identification of single dye labeled mononucleotide molecules released from and optical fiber in a microcapillary: First steps towards a new single molecule DNA sequencing technique" *Phys. Chem. Chem. Phys.* 1(10):2471-2477 (1999).
Shendure et al. "Accurate Multiplex Polony Sequencing of an Evolved Bacterial Genome" *Science* 309(5741):1728-1732 (2005).
Shendure et al. "Advanced sequencing technologies: methods and goals" *Nat. Rev. Genet.* 5:335-344 (2004).
Walter et al. "Do-it-yourself guide: how to use the modern single-molecule toolkit," *Nature Methods* 5(6):475-489 (2008).
Zhang et al. "Single-quantum-dot-based DNA nanosensor" *Nature Materials* 4:826-831 (2005).
Adessi, C. et al., "Solid phase DNA amplification: characterization of primer attachment and amplication mechanisms," Nucleic Acids Research, vol. 28, No. 20, e87 (2000).
Blackard, J. T. et al., "Intrahepatic cytokine expression is downregulated during HCV/HIV co-infection," Journal of Medical Virology, vol. 78, pp. 202-207 (2006).
Cao, Y.M. et al., "DNA-modified core-shell Ag/Au nanoparticles," J. Am. Chem. Soc., vol. 123, pp. 7951-7962 (2001).
Levin, J. D., "Position-dependent effects of locked nucleic acid (LNA) on DNA sequencing and PCR primers," Nucleic Acids Research, vol. 34, No. 20, e142 (2006).
Ozeoiak et al., "Direct RNA sequencing," Nature 461:814-818 (2009).
Qiu et al., "Fluorescence single-molecule counting assays for high-sensitivity detection of cytokines and chemikines," Clin. Chem. 53(11):2010-2012 (2007).
Tessier, D. C. et al., "Ligation of single-stranded oligodeoxyribonucleotides by T4 RNA ligase," Anal. Biochem., vol. 158, pp. 171-178 (1986).
Wang, T. et al., "Single-molecule tracing on a fluidic microchip for quantitative detection of low-abundance nucleic acids," JACS, vol. 127, pp. 5354-5359 (2005).
Guo et al. (2010) "An Integrated System for DNA Sequencing by Synthesis Using Novel Nucleotide Analogues" *Accounts of Chemical Research*, 43(4):551-63.
Turcatti et al. (2008) "A new class of cleavable fluorescent nucleotides: synthesis and optimization as reversible terminators for DNA sequencing by synthesis" *Nucleic Acids Res.*, 36(4):e25. doi: 10.1093/nar/gkn021, published online Feb. 7, 2008.
Abramova, T., et al., "Design and Synthesis of Dinucleotide 5'-triphosphates with Expanded Functionality", Biorganic & Medicinal Chemistry 16, pp. 9127-9132 (2008).
Yoo, Christine Bora, "Use of DNA Methylation Inhibitors for Chemotherapy and Chemoprevention of Cancer", Dissertation, University of Southern California, Aug. 2007.
Office Action mailed from Canadian Intellectual Property Office in corresponding Canadian Application No. 2,776,538, dated Apr. 21, 2015 (5 pages).
Patent Examination Report No. 1 dated Feb. 25, 2013, issued in Australian Patent Application No. 2011260786.
International Preliminary Report on Patentability dated Dec. 4, 2012 (including Written Opinion dated Sep. 15, 2011), issued in International Application No. PCT/CN2011/075106.
International Search Report dated Sep. 15, 2011, issued in International Application No. PCT/CN2011/075106.

\* cited by examiner

COMPOSITIONS AND METHODS FOR SEQUENCING NUCLEIC ACIDS

PRIORITY INFORMATION

This application claims priority to U.S. Application Ser. No. 61/350,693, filed Jun. 2, 2010.

TECHNICAL FIELD

The application relates to methods of determining the sequence of a nucleic acid. Further, the application relates to nucleotide analogs and their use in sequencing a nucleic acid.

BACKGROUND

A variety of techniques and processes have been developed to obtain genetic information, including broad genetic profiling or identifying patterns of discrete markers in genetic codes and nucleotide level sequencing of entire genomes. Knowledge of DNA sequences has become indispensable for basic biological research in numerous applied fields such as biotechnology, forensic biology, diagnostic, systematic biology, synthetic biology and personal healthcare. The advent of DNA sequencing has significantly accelerated biological research and discovery. While techniques have been developed to read, at the nucleotide level, a genetic sequence, such methods can be time-consuming and extremely costly.

Most current technologies of Next Generation Sequencing (reviewed in Metzker, M. L., NATURE REVIEWS GENETICS 11: 31-45 (2010)) have greatly lowered the cost of sequencing by shifting from electrophoresis-based methods to chip-based sequencing, which typically involves sequencing single target molecules instead of deriving sequence information from a population of amplified target molecules. The introduction of real-time sequencing, wherein the progression of successive nucleotide incorporation events is monitored while the nucleic acid polymerization process takes place, has also improved the efficiency of sequencing.

The common strategies for real-time single-molecule sequencing were derived from the concept of pyrosequencing, wherein the PP; moiety of nucleotide triphosphate monomers is labeled with a photo-detectable label. In pyrosequencing reactions, a photo-signal is released and detected during polymerase extensions as each monomer is incorporated into a growing chain (see, e.g., Ronaghi, et al., SCIENCE, 281: 363-365 (1998); Hyman, ANAL. BIOCHEM., 174: 423-436 (1988); and U.S. Pat. Nos. 6,255,083 and 7,329,492). A method of single-molecule detection using a zero-mode waveguide (ZMW) to increase the signal-to-noise ratio in single-molecule sequencing has also been described in U.S. Pat. Nos. 7,170,050 and 7,056,676.

In any enzyme-mediated, template-dependent sequencing process, the overall fidelity, processivity, and accuracy of the incorporation process can directly impact sequence determination. Lower accuracy of target sequence reads may require multiple-fold coverage to determine the sequence of a target with a high level of confidence. Despite the recent developments, a need exists for a sequencing scheme that provides greater accuracy per sequencing reaction.

SUMMARY OF CERTAIN EMBODIMENTS

Embodiments described herein provide novel methods for extending the observation duration of single-molecule signal detection to improve the accuracy of single-molecule sequence determination. Embodiments include a method of determining the nucleotide sequence of a target nucleic acid. In some embodiments, the method comprises the steps of: (a) providing a reaction complex comprising a template nucleic acid comprising a target nucleic acid sequence, a primer nucleic acid comprising a sequence which is complementary to a region of the template nucleic acid, and a polymerase enzyme or an enzyme complex comprising 5' to 3' polymerization activity and proofreading 3' to 5' exonuclease activity (b) contacting the reaction complex with a plurality of nucleotide analogs, wherein an individual nucleotide analog of said plurality comprises at least one base-pairing moiety and at least one label moiety comprising a photo-detectable label that is indicative of the identity of the base-pairing moiety; (c) allowing the enzyme or enzyme complex to incorporate a nucleotide analog in a template-dependent manner into a nascent strand via the enzyme's or enzyme complex's 5' to 3' polymerization activity, whereby the label moiety is coupled to the nascent strand; (d) detecting the photo-detectable label of the incorporated nucleotide analog; (e) allowing the enzyme or enzyme complex to remove the label moiety of the incorporated nucleotide analog from the nascent strand via the enzyme's or enzyme complex's proofreading 3' to 5' exonuclease activity; and (f) repeating steps (c)-(e) to determine the sequence of the target nucleic acid.

The methods described herein include a method of determining a nucleotide base incorporated by a polymerase enzyme or enzyme complex in a nucleic acid polymerization reaction, the method comprising the steps of: (a) conducting a nucleic acid polymerization reaction that utilizes both 5' to 3' polymerization activity and 3' to 5' exonuclease activity of a polymerase enzyme or enzyme complex, and that results in production of a nascent strand in a template-dependent manner, wherein said reaction is conducted in the presence of (i) a template nucleic acid comprising a target nucleic acid sequence, (ii) a primer nucleic acid comprising a sequence which is complementary to a region of the template nucleic acid, (iii) a polymerase enzyme or an enzyme complex comprising 5' to 3' polymerization activity and 3' to 5' exonuclease activity, (iv) a plurality of nucleotide analogs, wherein an individual nucleotide analog of said plurality comprises at least one base-pairing moiety and at least one label moiety, said label moiety comprising a photo-detectable label; and (b) detecting the photo-detectable label, wherein said label is indicative of the identity of the base or bases present in the nucleotide analog incorporated by the enzyme or enzyme complex into the nascent strand.

Embodiments further include a method of determining the nucleic acid sequence of a target nucleic acid sequence, the method comprising the steps of: (a) conducting a nucleic acid polymerization reaction in the presence of (i) a template nucleic acid comprising a target nucleic acid sequence, (ii) a primer nucleic acid comprising a sequence which is complementary to a region of the template nucleic acid, (iii) a polymerase enzyme or enzyme complex comprising a reaction site for incorporating a nucleotide analog in a template-dependent manner, (iv) a plurality of nucleotide analogs, wherein an individual nucleotide analog of said plurality comprises at least one base-pairing moiety and at least one label moiety comprising a photo-detectable label, and wherein the analog does not terminate production of a nascent strand once the analog is incorporated in a template-dependent manner by the enzyme or enzyme complex into the nascent strand, and wherein said nucleotide analog provides at least one of prolonged detection duration and prolonged interpulse duration as compared to a nucleotide analog comprising a label which is removed via the 5' to 3' polymerization activity of the enzyme or enzyme complex; and (b) detecting the label moiety incorporated during each successive incorporation event.

The photo-detectable label utilized in any of the sequencing methods described herein can be a fluorophore or any other suitable label detectable by a light detector. The nucleotide analog utilized in any of the methods described herein may comprise at least one fluorescence quenching moiety. The fluorescence quenching moiety may be removed from the nucleotide analog upon incorporation of the nucleotide analog via the enzyme's or enzyme complex's 5' to 3' polymerization activity in a template-dependent manner. In some aspects, the fluorescence quenching moiety is attached to the 5' end of a nucleotide analog, optionally via a linker. In some aspects, the fluorescence quenching moiety is attached to the beta or gamma phosphate of the triphosphate group at the 5' end of the nucleotide analog.

In some aspects, the label moiety comprises a photo-detectable label and an optional linker connecting the photo-detectable label to a phosphate linkage. In some other aspects, the label moiety comprises: (a) one or more non-complementary nucleotide residues; (b) a photo-detectable label; and (c) an optional linker connecting the photo-detectable label to the one or more non-complementary nucleotide residues. The one or more non-complementary nucleotide residues can be independently chosen from an abasic nucleotide residue and a nucleotide residue comprising a base which lacks substantially the ability to base pair with any of adenine, cytosine, guanine, thymine, or uracil.

The base-pairing moiety of the nucleotide analog typically comprises a base that is able to base pair with a corresponding base of the template nucleic acid in an incorporation site of the reaction complex. In some aspects, the 3' end of the base-pairing moiety is connected to the label moiety via a phosphate linkage. In some aspects, base-pairing moiety comprises at least three phosphate groups at its 5' end, wherein the phosphate group most proximal to the base-pairing moiety (the alpha phosphate) is a phosphorothioate, methylphosphonate, or boranophosphate.

Embodiments further include a compound having Formula I:

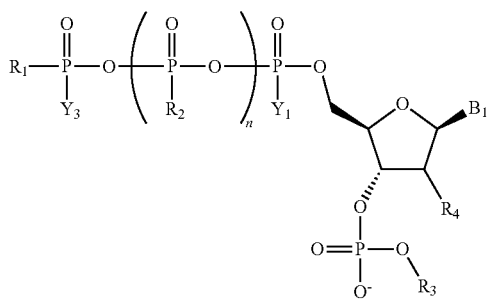

Formula I or a pharmaceutically acceptable salt or hydrate thereof, wherein n is 1, 2, 3, 4, 5, 6, 7, 8, or 9;

$R_1$ and each $R_2$ is chosen from $O^-$ and

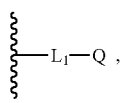

wherein
i) $R_1$ and each $R_2$ are $O^-$; or
ii) $R_1$ is

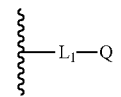

and each $R_2$ is $O^-$; or
iii) $R_1$ is $O^-$, one $R_2$ is

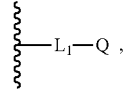

and any remaining $R_1$ is independently $O^-$, $S^-$, $BH_3^-$, or $CH_3$;

$R_3$ is a nucleotide moiety comprising a fluorescent dye F;

$R_4$ is H, OH, halogen (including fluorine, chlorine, bromine, and iodine), alkyl (including $CH_3$, $CH_2CH_3$) or alkoxy (both substituted and unsubstituted) (including $OCH_3$ and $OCH_2CH_3$);

$Y_1$, and $Y_3$ are each independently chosen from $O^-$, $S^-$, $BH_3^-$, and $CH_3$;

$L_1$ is chosen from alkyl, alkenyl, alkynyl, aryl, heteroaryl, heterocyclyl, ester, amino, and sulfonyl;

Q is a fluorescence quenching moiety; and $B_1$ is chosen from adenine, cytosine, guanine, thymine, uracil, hypoxanthine, and 5-methylcytosine.

The methods can be performed under conditions whereby the length of time between binding of the nucleotide analog at the incorporation site of the reaction complex and removal of the label moiety from the nascent strand is from about 50 to 250 milliseconds, or any other range that is described herein.

The methods can also be performed under conditions whereby the length of time between two successive detecting steps is from about 0.2 seconds to 1 second, about 0.2 to 0.6 seconds, about 0.3 to 0.5 seconds, or any other range disclosed herein.

Further provided is an apparatus suitable for carrying out the sequencing method disclosed herein. This apparatus includes a detector or a detector system disclosed herein and a support on which the reaction complex is placed.

It is to be understood that both the foregoing general description and the following detailed description are exemplary and explanatory only and are not restrictive of the embodiments, as claimed.

The accompanying drawings, which are incorporated in and constitute a part of this specification, illustrate several embodiments of the invention and together with the description, serve to explain the principles thereof.

DETAILED DESCRIPTION OF THE EMBODIMENTS

1. Methods

Figure 1:
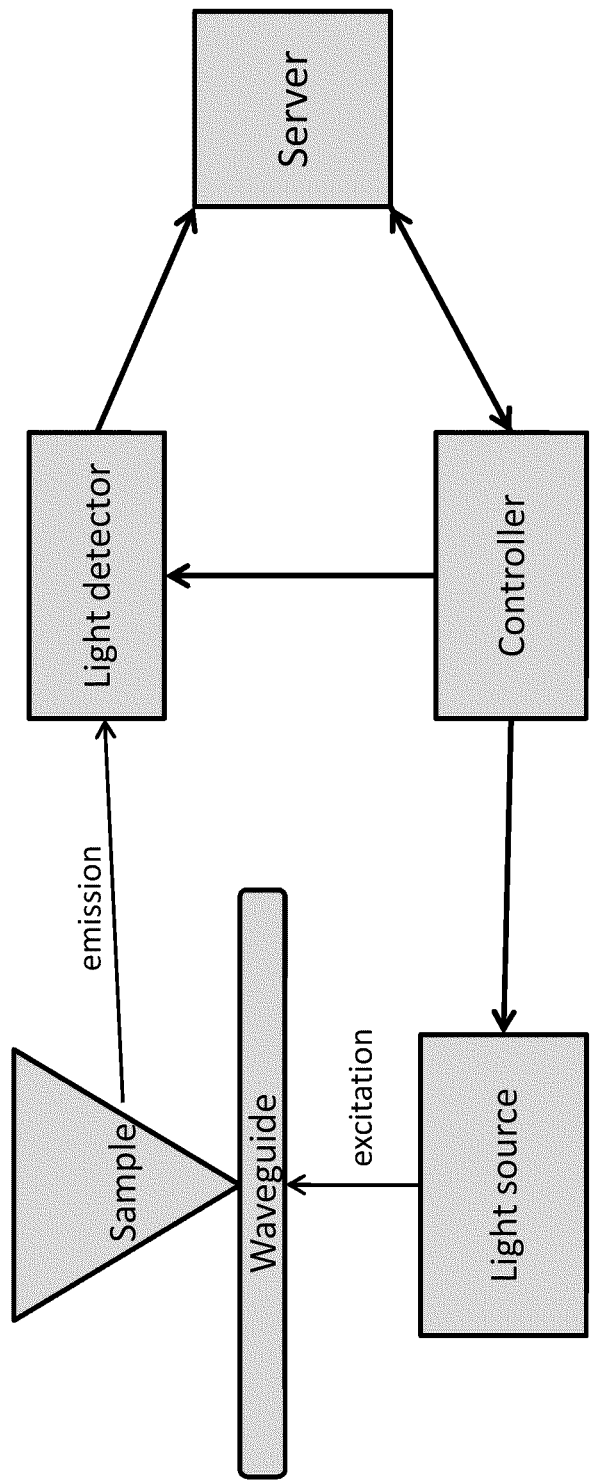
FIG. 1 depicts a general schematic of an embodiment of a detection system that may be used as described herein.

The compositions and methods disclosed herein provide an effective means for conducting single molecule sequencing, particularly real-time single molecule sequencing. The sequencing procedures provided herein may embody one or more of the following unique features. First, the detection duration during which a signal from the nucleotide being incorporated in a template-dependent manner by a polymerase enzyme or an enzyme complex may be prolonged. This can be achieved by, e.g., utilizing a labeled but non-terminating nucleotide analog, whose label may stay with the incorporated nucleotide residue and remain as part of the nascent strand until it is cleaved by the enzyme or enzyme complex prior to incorporation of the next base. Second, the signal pulses corresponding to successive nucleotide incorporation events may be further separated in time by a prolonged interpulse duration (e.g., a "no-signal" or "dark" period). This can be achieved by, e.g., taking advantage of the time required by an enzyme or enzyme complex to switch from 3' to 5' exonuclease activity to 5' to 3' polymerization activity. The combination of these two attributes may provide a longer "signal" period for a detector to sense an incorporation event and a clear "no signal" or "dark" period between each consecutive incorporation events to allow a detector to accurately register the completion of an incorporation event.

Accordingly, embodiments include a method of determining the nucleotide sequence of a target nucleic acid. In some embodiments, the method comprises the steps of: (a) providing a reaction complex comprising a template nucleic acid comprising a target nucleic acid sequence, a primer nucleic acid comprising a sequence which is complementary to a region of the template nucleic acid, and a polymerase enzyme or an enzyme complex comprising 5' to 3' polymerization activity and proofreading 3' to 5' exonuclease activity (b) contacting the reaction complex with a plurality of nucleotide analogs, wherein an individual nucleotide analog of said plurality comprises at least one base-pairing moiety and at least one label moiety comprising a photo-detectable label that is indicative of the identity of the base-pairing moiety; (c) allowing the enzyme or enzyme complex to incorporate a nucleotide analog in a template-dependent manner into a nascent strand via the enzyme's or enzyme complex's 5' to 3' polymerization activity, whereby the label moiety is coupled to the nascent strand; (d) detecting the photo-detectable label of the incorporated nucleotide analog; (e) allowing the enzyme or enzyme complex to remove the label moiety of the incorporated nucleotide analog from the nascent strand via the enzyme's or enzyme complex's proofreading 3' to 5' exonuclease activity; and (f) repeating steps (c)-(e) to determine the sequence of the target nucleic acid.

Embodiments further include a method of determining a nucleotide base incorporated by a polymerase enzyme or enzyme complex in a nucleic acid polymerization reaction, the method comprising the steps of: (a) conducting a nucleic acid polymerization reaction that utilizes both 5' to 3' polymerization activity and 3' to 5' exonuclease activity of a polymerase enzyme or enzyme complex, and that results in production of a nascent strand in a template-dependent manner, wherein said reaction is conducted in the presence of (i) a template nucleic acid comprising a target nucleic acid sequence, (ii) a primer nucleic acid comprising a sequence which is complementary to a region of the template nucleic acid, (iii) a polymerase enzyme or an enzyme complex comprising 5' to 3' polymerization activity and 3' to 5' exonuclease activity, (iv) a plurality of nucleotide analogs, wherein an individual nucleotide analog of said plurality comprises at least one base-pairing moiety and at least one label moiety, said label moiety comprising a photo-detectable label; and (b) detecting the photo-detectable label, wherein said label is indicative of the identity of the base or bases present in the nucleotide analog incorporated by the enzyme or enzyme complex into the nascent strand.

Embodiments further include a method of determining the nucleic acid sequence of a target nucleic acid sequence, the method comprising the steps of: (a) conducting a nucleic acid polymerization reaction in the presence of (i) a template nucleic acid comprising a target nucleic acid sequence, (ii) a primer nucleic acid comprising a sequence which is complementary to a region of the template nucleic acid, (iii) a polymerase enzyme or enzyme complex comprising a reaction site for incorporating a nucleotide analog in a template-dependent manner, (iv) a plurality of nucleotide analogs, wherein an individual nucleotide analog of said plurality comprises at least one base-pairing moiety and at least one label moiety comprising a photo-detectable label, and wherein the analog does not terminate production of a nascent strand once the analog is incorporated in a template-dependent manner by the enzyme or enzyme complex into the nascent strand, and wherein said nucleotide analog provides at least one of prolonged detection duration and prolonged interpulse duration as compared to a nucleotide analog comprising a label which is removed via the 5' to 3' polymerization activity of the enzyme or enzyme complex; and (b) detecting the label moiety incorporated during each successive incorporation event.

Embodiments encompass the use of nucleotide analogs as nucleotide substrates for sequencing by synthesis, wherein the analogs may comprise (i) a base-pairing moiety at the 5' end of the analog, comprising one or more nucleotide residues that each comprise a base that is able to base pair with a corresponding base of a target nucleic acid in an incorporation site of a nucleic acid polymerizing reaction complex, and (ii) a label moiety to the 3' end of the base-pairing moiety via, e.g., a phosphate linkage, wherein the label moiety is non-complementary with the target strand and comprises a photo-detectable label. A polymerase enzyme or an enzyme complex according to the present invention may incorporate a nucleotide analog into a growing strand by template-dependent replication, whereby the base-pairing moiety at the 5' end of the analog base pairs with one or more corresponding bases of the template strand, and association of the analog with the enzyme and incorporation of the analog into the replicating strand is detected via the photo-detectable label on the label moiety of the analog. Detection of the photo-detectable label may continue until the label moiety, which comprises the photo-detectable label and which is unable to base pair with the target strand, is excised by the proofreading 3' to 5' exonuclease activity of the polymerizing enzyme. Thus, detection of the photo-detectable label may be prolonged without decreasing the concentration of nucleotide analog substrates to slow the rate of the synthesis reaction. The enzyme or enzyme complex may then proceed to the next step of synthesis, where it may incorporate another analog comprising a base-pairing moiety at its 5' end which base pairs with the following one or more bases of the template strand. The sequencing accuracy is increased by the prolonged signal to differentiate from the noise caused by transient association of labeled reactants during the synthesis reaction. The length of time a signal is visible from a labeled reactant remaining associated with a polymerizing complex may be equivalent to the length of time in which a polymerase can switch from polymerizing activity to exonuclease activity and cleave a mismatched nucleotide residue. In some embodiments, the length of time between binding of a nucleotide analog to the incorporation site of a nucleic acid-synthesizing reaction complex and removal of the label moiety of the analog from the nascent ("primer") strand is from about 50 to 250 milliseconds. In some embodiments, the length of time is less than 50 milliseconds, or greater than 250 milliseconds.

1.1 Sequenceing Complex and Related Material

Practice of the methods provided herein typically involve a reaction mixture comprising a polymerase enzyme or enzyme complex, a template nucleic acid comprising a target nucleic acid sequence, a primer, and one or more types of nucleotide analogs. Various buffers and metal ions suitable for a polymerization reaction can also be utilized.

As used herein, a "sequencing complex" or "reaction complex" (used interchangeably) refers to a complex comprising a polymerase enzyme or an enzyme complex, a template molecule, and a primer molecule. A sequencing complex may be attached to a solid support. Attachment may occur through one or more components of the sequencing complex, including the polymerase, the template molecule, the primer molecule, or indirectly through a molecule associated with any component of the sequencing complex, as described in further detail below.

Where desired, the polymerase can be left in solution or immobilized on a support. The polymerase can be immobilized on a support by any method known in the art, such as by direct adsorption, affinity binding, and covalent or non-covalent linkage through tethering molecules. Some non-limiting examples of such tethering linkages are biotin-streptavidin, antibody-haptene, lectin-saccharide, silane coupling, carbodiimide, maleimide, peptide, carbohydrate, ester, substituted ester, anhydride, substituted anhydride, and polylactide linkages. There are many tethering molecules that may be used which have been widely described in the art. Some non-limiting examples include: dithiothreitol, disuccinimidyl glutarate, disuccinimidyl suberate, bis(sulfo-succinimidyl)suberate, dithiobis(succinimidylpropionate), dithiobis(sulfosuccinimidylpropionate), ethylene glycobis (succinimidylsuccinate), ethylene glycobis (sulfosuccinimidylsuccinate), disuccinimidyl tartrate, disulfosuccinimidyl tartrate, bis[2-(succinimidyloxycarbonyloxy)ethyl]sulfone, bis[2-(sulfosuccinimidooxycarbonyloxy)ethyl]sulfone, succinimidyl 4-(N-maleimido-methyl)cyclohexane-1-carboxylate, sulfo-succinimidyl 4-(N-maleimidomethyl)cyclohexane-1carboxylate, m-Maleimidobenzoyl-N-hydroxysuccinimide ester, m-maleimidobenzoyl-N-hydroxysulfosuccin imide ester, succinimidyl 4-(p-maleimido-phenyl)-butyrate, sulfosuccinimidyl 4-(p-maleimidophenyl)-butyrate, bismaleimidohexane, N-(y-maleimidobutyryloxy)succinimide ester, N-(y-maleimidobutyryloxy)sulfosuccinimide ester, N-succinimidyl(4-iodoacetyl)aminobenzoate, sulfosuccinimidyl(4-iodoacetyl)-aminobenzoate, 1,4-di-[3'-2'-pyridyl-dithio(propionamido)butane], 4-succinimidyloxycarbonyl-a-(2-pyridyldithio)toluene, sulfosuccinimidyl-6-[a-methyl-a-(2-pyridyldithio)-toluamido]hexanoate, N-succinimidyl-3 (2-pyridyldithio)-propionate, succinimidyl 6-[3-(2-pyridyldithio)-propionanido]hexanoate, sulfosuccinimidyl-6-[-3-(2-pyridyldithio)-propionamido]hexanoate, 3-(2-pyridyldithio)-propionyl hydrazide, 1-ethyl-3-(3-dimethylaminopropyl)-carbodiimide hydrochloride, N,N'-dicyclohexylcarbodiimide, 4-(p-azidosalicylamido)-butylamine, azidobenzoyl hydrazide, N-5-azido-2-nitrobenzoyloxysuccinimide, N-[4-(p-azidosalicylamido) butyl]-3'(2'-pyridyldithio)propionamide, p-azidophenyl glyoxal monohydrate, 4-(p-azidosalicylamido)butylamine, 1-(p-azidosalicylamido)-4-(iodoacetamido)butane, bis-[(3-4-azidosalicylamido)ethyl]disulfide, N-hydroxysuccinimidyl-4-azidobenzoate, n-hydroxysulfo-succinimidyl4-azido-benzoate, N-hydroxysuccinimidyl-4-azidosalicylic acid, N-hydroxysulfosuccinimidyl-4-azidosalicylic acid, sulfosuccinimidyl-(4-azidosalicylamido)-hexanoate, p-nitrophenyl-2-diazo-3,3,3-trifluoropropionate, 2-diazo-3,3,3,-trifluoro-propionylchloride, N-succinimidyl-(4-azidophenyl) 1,3'-dithiopropionate, sulfosuccinimidyl-(4-azidophenyldithio)propionate, sulfosuccinimidyl-2-(7-azido-4-methylcoumarin-3-acetamide)ethyl-1,3'-dithiopropionate, sulfosuccinimidyl 7-azido-4-methylcoumarin-3-acetate, sulfosuccinimidyl 2-(m-azido-onitrobenzamido)-ethyl-1,3'-dithio propionate, N-succinimidyl-6-(4'-azido-2'-nitrophenylamino)hexanoate, sulfosuccinimidyl 6-(4'-azido-2'-nitrophenylamino)hexanoate, sulfosuccinimidyl 2-(pazidosalicylamido)ethyl-1,3'-dithiopropionate, sulfosuccinimidyl 4-(p-azidophenyl)-butyrate.

The polymerase may be immobilized on any support that does not interfere with a nucleic acid polymerization reaction. The material, shape, and/or size of the support may depend on the detection system that is used to detect the signals from the reaction complex. A wide variety of support can be utilized including, without limitation, those made of metals, metal oxides, silicon, glass, quartz, polymers, carbohydrates, resins, and any composites thereof. The materials may be positively charged, negatively charged, or contain no charge, and may be unmodified or derivatized with a coating to aid in complex immobilization. The supports may further be of any suitable shape and size, which include but are not limited to plates, beads, spheres, slides, wafers, chips, and the surfaces of various containers, including wells, capillaries, pipettes, channels, tubes, pores, cuvettes, and microfluidic channels, chambers, and wells. Supports can adopt any suitable formats, including but not limited to multiwell plates and arrays of nano-sized wells. Immobilization of the polymerase may serve to localize the polymerase within a confined space for imaging, such as within attoliter or zeptoliter scale volumes for zero mode waveguide imaging.

The polymerase may be attached to the support through the polymerase subunit, or through any other subunit contained in the polymerase. The polymerase may contain a subunit that serves no function other than to attach the polymerase to the immobilizing support. Polymerases may be immobilized randomly on the support, in arrays, or in any other pattern on the support surface.

Any polymerase possessing 5' to 3' polymerization and 3' to 5' exonuclease activity can be utilized in the sequencing methods disclosed herein. The term "3' to 5' exonuclease activity" refers to the hydrolytic cleavage of the phosphodiester bond at the 3' end of a nascent strand. 3' to 5' exonuclease activity can be utilized for error-correcting (i.e., proofreading) a base incorporated into a nascent (i.e., growing) strand. Typically, the term is used in reference to a template-specific nucleic acid polymerase whereby nucleotides that do not form Watson-Crick base pairs with the template are removed from the 3' end of a nascent strand in a sequential manner. Examples of polymerases that have error-correcting activity include but are not limited to polymerases from *Pyrococcus furiosus, Thermococcus litoralis*, and *Thermotoga maritime*. A "mismatched nucleotide" or a "mismatch" refers to a nucleotide that is not complementary to the target nucleic acid sequence at that position.

The term "polymerase" as used herein refers to an enzyme or an enzyme complex that catalyzes polynucleotide synthesis by addition of nucleotide units to a nucleotide chain using DNA or RNA as a template. The term encompasses monomeric and multimeric enzyme (e.g., an enzyme complex). An enzyme complex may comprise a single enzyme or multiple enzymes, and may also include additional non-enzymatic proteins or other subunits. For instance, the two types of enzymatic activities can be carried out by one or more subunits of an enzyme complex. The complex may be held together through noncovalent associations between subunits (e.g., via hydrogen bonding, ionic bonding, Van der Waals force, and hydrophobic interactions) or covalent association (e.g., via disulfide bonds or lactam bridges). Some non-limiting examples of such complexes may include at least one catalytic subunit of a nucleic acid polymerase, including wild-type, recombinant, mutant, and engineered polymerase. Generally, the polymerase will initiate synthesis at the 3' end of a primer annealed to a polynucleotide template sequence, and will proceed toward the 5' end of the template strand. A "DNA polymerase" catalyzes the polymerization of deoxynucleotides. An "RNA polymerase" catalyzes the polymerization of ribonucleotides.

As noted above, some polymerases may also possess proofreading activity such as the 3' to 5' exonuclease activity within the same subunit that carries out the 5' to 3' polymerization activity. This class of polymerases include without limitation prokaryotic DNA pol I, II, and III, eukaryotic DNA pol $\alpha$, $\delta$, and $\epsilon$, and phage replicases.

A proofreading polymerase has the ability to catalyze the template-directed synthesis of DNA from deoxyribonucleotide (or RNA from ribonucleotide), and also a 3' to 5' proofreading exonuclease activity and thus can excise a mismatched nucleotide at or near the 3' terminus of a nascent strand when it is hybridized to the template. In some embodiments, the 5' to 3' polymerase activity and the 3' to 5' exonuclease reside in separate subunits of a polymerase complex, such as the $\alpha$ and $\epsilon$ subunits of *E. coli* DNA polymerase III complex, respectively (A. Kornberg & T. A. Baker, "DNA Replication", Second Edition, University Science Books, U.S.A., 2005). In some embodiments, the proofreading polymerase is Pfu, KOD, Tgo, Vent, Deep Vent, phi29 DNA polymerase, T4 DNA Polymerase (see, e.g., Reha-Krantz, L. J., GENETICS, 148: 1551-1557 (1998)), or T7 DNA polymerase. Suitable proofreading enzymes may be B type polymerases. B type polymerases may be thermostable polymerases, such as *Pyrococcus* polymerases, e.g., Pfu, Pwo, Pho, Pab, Pko, Pgl polymerases; *Thermococcus* polymerases, e.g., *Thermococcus litoralis, Thermococcus barossii*, and *Thermococcus gorgonarius* polymerases; and polymerases from *Pyrodictium* spp. Thermostable polymerases having 3' to 5' exonuclease activity can also be isolated from eubacterial strains such as *Thermotoga*. The polymerase may also be derived from a natural polymerase and engineered to possess both 5' to 3' polymerase and 3' to 5' exonuclease activity, wherein the modified 3' to 5' exonuclease activity is able to hydrolytically cleave a label moiety $R_3$ of Formula 1 described above, wherein the $R_3$ does not comprise nucleotide moieties or nucleotide analog structures.

Useful nucleic acid polymerases may be non-thermostable or thermophilic. A thermophilic polymerase (also referred to as "thermally stable" or "thermostable" polymerase) refers to any enzyme that catalyzes polynucleotide synthesis by addition of nucleotide units to a nucleotide chain using DNA or RNA as a template, that has an optimal activity at a temperature above 45° C., and does not irreversibly denature at high temperatures, such as above 90° C. Non-limiting examples of thermostable polymerases are Taq and Pfu DNA polymerase and their derivatives, as well as those from thermophilic organisms such as *Thermus aquaticus, Thermus thermophilus, Thermococcus litoralis, Bacillus sterothermophilus, Thermotoga maritime*, and other *Thermus, Bacillus, Thermotoga*, and *Pyrococcus* species. Thermostable polymerases also include and are not limited to those from thermophilic bacteriophages, such as Pyro-Phage 3173 DNA polymerase (Lucigen).

In some embodiments, the polymerase is a non-thermostable polymerase, including but not limited to, phi29 and BST DNA polymerase. Another illustrative example is the large fragment of *E. coli* DNA Polymerase I (Klenow), which has 3' to 5' exonuclease activity and lacks 5' to 3' exonuclease activity. This enzyme or equivalent enzymes can be used in embodiments where the synthesis reaction is not performed at high temperatures, such as during isothermal PCR. In some embodiments, the polymerase is an archaeal DNA polymerase.

Complexes suitable for the invention may also contain polymerases that lack 3' to 5' exonuclease activity, including polymerases that naturally lack exonuclease activity such as certain RNA polymerases, reverse transcriptases, as well as polymerases that have been truncated or otherwise modified to not contain exonuclase activity. Such enzyme complexes when used in the present invention typically further comprise an additional subunit that is capable of performing the 3' to 5' exonuclease activity.

Polymerases suitable for this invention may also possess strand displacement activity, which refers to the ability of the polymerase to displace downstream DNA during polymerization. Strand-displacing polymerases may have reduced or essentially no 5' to 3' exonuclease activity. On a circular template molecule, strand-displacing polymerases may produce tandem repeats of the template sequence, effectively resequencing the same template. This is particularly advantages for single molecule sequencing as the sequence information can be repeatedly derived from the same molecule in a tandem fashion. Non-limiting examples of strand-displacing polymerases suitable for the present invention include but are not limited to Phi29 DNA polymerase, Bst DNA polymerase, T5 DNA polymerase, T4 DNA polymerase holoenzyme, phage M2 DNA polymerase, phage PRD1 DNA polymerase, and the Klenow fragment of DNA polymerase I.

In some embodiments, the polymerase is a hybrid protein comprising a polymerization domain and a 3' to 5' exonuclease. The term "hybrid protein" is used herein to describe a protein that comprises amino acid residues from multiple parent sequences. Examples of hybrid polymerase proteins and methods of generating hybrid proteins are disclosed in International Pat. Pub. No. WO 2004/011605. Such polymerases are therefore non-naturally occurring variants of polymerases.

In some embodiments, it is advantageous to use polymerases having enhanced processivity. Examples of these include polymerases described in International Pat. Pub. No. WO 01/92501 and U.S. Pat. No. 7,666,645. These improved polymerases exhibit enhanced processivity due to the presence of a sequence-non-specific double stranded DNA binding domain that is joined to the polymerase or the enzymatic domain of the polymerase. In some embodiments, the binding domain is from a thermostable organism and provides enhanced activity at higher temperatures, e.g., temperatures above 45° C. For example, Sso7d and Sac7d are small (about 7,000 kd MW), basic chromosomal proteins from the hyperthermophilic archaeabacteria *Sulfolobus solfataricus* and *S. acidocaldarius*, respectively (see, e.g., Choli et al., BIOCHIMICA ET BIOPHYSICA ACTA 950: 193-203 (1988); Baumann et al., STRUCTURAL BIOL. 1: 808-819 (1994); and Gao, et al., NATURE STRUC. BIOL. 5: 782-786 (1998)). These proteins bind DNA in a sequence-independent manner and when bound, increase the Tm of DNA by up to 40° C. under some conditions (McAfee et al., BIOCHEMISTRY 34:10063-10077 (1995)). These proteins and their homologs may be used as the sequence-non-specific DNA binding domain in improved polymerase fusion proteins. Sso7d, Sac7d, Sac7e and related sequences (referred to herein as "Sso7 sequences" or "Sso7 domains") are known in the art (see, e.g., accession numbers (P39476 (Sso7d); P13123 (Sac7d); and P13125 (Sac7e)). Other sequence non-specific double stranded nucleic acid binding proteins are topoisomerase, helicase, or PCNA. Additional examples are described in Motz, et al., J. BIOL. CHEM. 277: 16179-88 (2002); Pavlov, et al., PROC. NATL. ACAD. SCI. USA, 99: 13510-13515 (2002)).

Suitable nucleic acid polymerases include functional fragments of nucleic acid polymerases. A "functional fragment" of a polymerase refers to any portion of a wild-type or mutant polymerase that encompasses less than the entire amino acid sequence of the polymerase and which retains the ability, under at least one set of conditions, to catalyze the polymerization of a polynucleotide and to excise a mismatched nucleotide via proofreading 3' to 5' exonuclease activity.

Other embodiments of the invention may use complexes that utilize other mechanisms for synthesizing the nascent strand, such as template-mediated ligation, or may add complementary nucleosides through a non-phosphodiester linkage, such as through forming a peptide bond. For the purposes of this invention, such methods of synthesis are also considered to be 5' to 3' polymerization.

In some embodiments, nucleic acid synthesis of the invention may be enhanced by the addition of other factors, including but not limited to proteins such as helicases, single-stranded DNA binding proteins, adenovirus DNA-binding protein, the HSV protein ICP8, and the BMRF1 polymerase accessory subunit.

1.2 Sequencing Primer

A sequencing primer is an oligonucleotide complementary to a segment of the nucleic acid to be detected or its associated end link primer which is capable of serving as a point of initiation for nucleic acid synthesis by the polymerase. In some embodiments, the sequencing primer may be at least 8, 10, 15, 20, 25, 30, 35, 40, 45, 50 nucleotides, or more in length. In particular embodiments, the sequencing primer may be from 8 to 25, from 10 to 20, from 10 to 30, or from 10 to 50 nucleotides in length. The sequencing primer may be made up of any type of nucleotide, including naturally-occurring nucleotides, nucleotide analogs not existing in nature, or modified nucleotides.

Primers are preferably single-stranded for maximum efficiency during amplification, but may also be double-stranded, either by self-annealing, e.g. "hairpin" primers, or by being annealed to another complementary sequence. Such double-stranded primers are particularly useful for embodiments that utilize "hot start" PCR.

In some embodiments, a sequencing primer may contain modified nucleotides, e.g., locked nucleic acids (LNAs; modified ribonucleotides, which provide enhanced base stacking interactions in a polynucleic acid). As an illustration of the utility of LNAs, Levin et al. (NUCLEIC ACID RESEARCH 34(20):142 (2006)) showed that a LNA-containing primer had improved specificity and exhibited stronger binding relative to the corresponding unlocked primer. Three variants of the MCP1 primer (5'-cttaaattttcttgaat-3') containing 3 LNA nucleotides (in caps) at different positions in the primer were made: MCP1-LNA-3'(5'-cttaaattttCtTgaAt-3'); MCP1-LNA-5' (5'-CtTaAattttcttgaat-3'); and MCP1-LNA-even (5'-ctTaaatTttctTgaat-3'). All LNA-substituted primers had enhanced Tm, while the MCP1-LNA-5' primer exhibited particularly enhanced sequencing accuracy (Phred Q30 counts). Accordingly, in particular embodiments, the sequencing primer may contain at least one locked nucleotide in its 5' region, i.e., the 5' half, third, or quarter of the sequencing primer. In some embodiments, primers may contain additional molecular groups, including but not limited to a detectable label, a 5' blocking group, or binding domains to recruit polymerase or other enzymes.

The sequencing primer and sample nucleic acid may be hybridized by mixing the sample nucleic acid with a molar excess of sequencing primer in a salt-containing solution, such as 10 mM Tris-HCl, pH 7.5, 1 M NaCl, and 1 mM EDTA buffer. The mixture may be heated to 65° C. for at least 5 minutes and slowly cooled to room temperature, to allow primer/template annealing. Residual primers may be eliminated by appropriate means including, e.g., a molecular sieve.

Primers, including both end link and sequencing primers, may be designed by appropriate means, including visual inspection of the sequence or computer-assisted primer design. Numerous software packages are available to assist in the primer design, including DNAStar™ (DNAStar, Inc., Madison, Wis.), OLIGO 4.0 (National Biosciences, Inc.), Vector NTI® (Invitrogen), Primer Premier 5 (Premierbiosoft), and Primer3 (Whitehead Institute for Biomedical Research, Cambridge, Mass.). Primers may be designed taking into account, for example, the molecule to be sequenced, specificity, length, desired melting temperature, secondary structure, primer dimers, GC content, pH and ionic strength of the buffer solution, and the enzyme used (i.e., polymerase or ligase). See, e.g., Sambrook and Russell, MOLECULAR CLONING: A LABORATORY MANUAL, Cold Spring Harbor Laboratory Press; 3rd edition (2001). In some embodiments, primers may consist of a mixture of different sequences, such as for multiplex PCR or when amplifying a template molecule with an unknown sequence. In the latter case, primer design may be unnecessary, and a mix of random sequences may be used for the primers instead.

1.3 End Link Primer

In some embodiments, a linear nucleic acid may further comprise one or more end link primers coupled to the 5' end, the 3' end, or both the 5' end and the 3' end of the nucleic acid. In particular embodiments, an end link primer may be affixed to the 3' end of the nucleic acid. End link primers may be used to provide a complementary sequence for a sequencing primer.

End link primers are short nucleic acid molecules usually composed of less than 100 nucleotides. In some embodiments, the end link primer may be at least 5, 10, 15, 20, 25, 30, 50, 75, 90 nucleotides, or more, in length. In certain embodiments, end link primers may be from 8 to 25, from 10 to 20, from 10 to 30, or from 10 to 50 nucleotides in length. In some embodiments, the end link primers may be unbranched, however, in other embodiments, they may be branched.

The end link primer may serve as a complement to a sequencing primer. In some embodiments, the 5' end of the end link primer may comprise a sequence complementary to a sequencing primer. In some embodiments, the end link primer sequence that is complementary to the sequencing primer may be oriented so that the 3' end of the sequencing primer may be immediately adjacent to the first nucleotide in the nucleic acid to be sequenced.

In some embodiments, end link primers may be added to ends of the nucleic acid to be detected by a ligase, for example, a DNA ligase. In some embodiments, the end link primer and nucleic acid to be detected may be both single stranded before the ligation. In other embodiments, both may be double stranded. In still other embodiments, one may be single stranded and the other may be double stranded. Ligation is well known in the art. For example, in the polony sequencing method, Shendure et al. (SCIENCE, 309:1728-1732 (2005)) ligated a T30 end link primer (32 bp) to a sample DNA segment with the New England Biolabs' (NEB) Quick Ligation kit. There, the ligation reaction solution included 0.26 pmole of DNA, 0.8 pmole of T30 end link primer, 4.0 µl T4 DNA Ligase, in 1× Quick Ligation Buffer. After mixing, the reaction solution was incubated for about 10 minutes at room temperature, and then placed on ice. The ligation reaction was stopped by heating the samples to 65° C. for 10 minutes.

In other embodiments, the end link primer may be synthesized on the nucleic acid to be sequenced. For example, the end link primer may be a homopolymer added by, e.g., terminal transferase. For example, Harris et al., (SCIENCE 320:106-109 (2008)) added a poly-A tail to DNA templates, which served as the complement to a poly-T sequencing primer in the single-molecule sequencing of a viral genome.

1.4 Nucleotide Analogs

Embodiments encompass the use of nucleotide analogs as substrates for nucleic acid sequencing by synthesis. In some embodiments, the individual analog comprises a base-pairing moiety and a label moiety. The base-pairing moiety may comprise one or more nucleotide residues at the 5' end of the analog that each comprises a base (e.g., adenine, cytosine, guanine, thymine, uracil, hypoxanthine, or 5-methylcytosine) that is able to base pair with a corresponding base of a template nucleic acid strand in an incorporation site of a reaction complex. The label moiety of the analog may be connected to the 3' end of the base-pairing moiety via a phosphate linkage, wherein the label moiety is chosen from (1) a photo-detectable label and an optional linker connecting the photo-detectable label to the phosphate, and (2) a group comprising one or more non-complementary nucleotide residues, a photo-detectable label, and an optional linker connecting the photo-detectable label to the one or more non-complementary nucleotide residues. The term "non-complementary" as applied to a nucleotide analog means that the nucleotide lacks substantially the ability to form Watson-Crick base pairs (e.g., the pairing of A-T, C-G, or A-U) with a corresponding base in the template sequence. Non-complementary nucleotide analogs include but are not limited to abasic nucleotide residues and nucleotide residues comprising a base which lacks substantially the ability to base pair with any of adenine, cytosine, guanine, thymine, or uracil. The non-complementary nucleotide residues can result in a "mismatch" ("mismatched nucleotide") which is subsequently cleaved via 3' to 5' exonuclease activity of a polymerase of the present invention.

Embodiments encompass the use of a plurality of nucleotide analogs, an individual analog of the plurality having a structure as shown in Formula I:

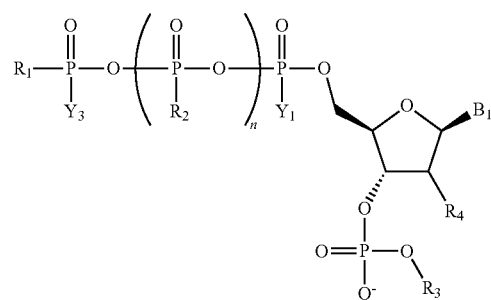

Formula I or a pharmaceutically acceptable salt or hydrate thereof, wherein
n is 1, 2, 3, 4, 5, 6, 7, 8, or 9;
$R_1$ and each $R_2$ is chosen from $O^-$ and

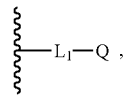

wherein
i) $R_1$ and each $R_2$ are $O^-$; or
ii) $R_1$ is

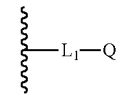

and each $R_2$ is $O^-$; or iii) $R_1$ is $O^-$, one $R_2$ is

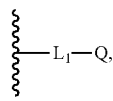

and any remaining $R_2$ is independently $O^-$, $S^-$, $BH_3^-$, or $CH_3$;

$R_3$ is a nucleotide moiety comprising a fluorescent dye F;

$R_4$ is H, OH, halogen (including fluorine, chlorine, bromine, and iodine), alkyl (including $CH_3$, $CH_2CH_3$) or alkoxy (both substituted and unsubstituted) (including $OCH_3$ and $OCH_2CH_3$);

$Y_1$, and $Y_3$ are each independently chosen from $O^-$, $S^-$, $BH_3^-$, and $CH_3$;

$L_1$ is chosen from alkyl, alkenyl, alkynyl, aryl, heteroaryl, heterocyclyl, ester, amino, and sulfonyl;

Q is a fluorescence quenching moiety; and

B1 is chosen from adenine, cytosine, guanine, thymine, uracil, hypoxanthine, and 5-methylcytosine.

In one embodiment, for example, n is 1, 2, 3, 4, 5, or 6. In some embodiments, n is 1, 2, 3, or 4. For example, n is 1, 2 or 3. In certain embodiments, n is 1.

Nucleotide moieties suitable as $R_3$ groups include mono-, di- and trinucleotides. In some embodiments, $R_3$ is chosen from: F,

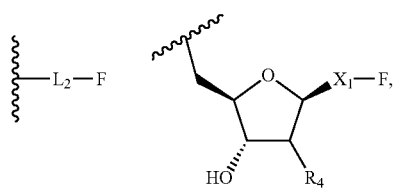

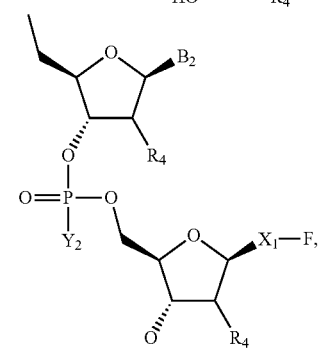

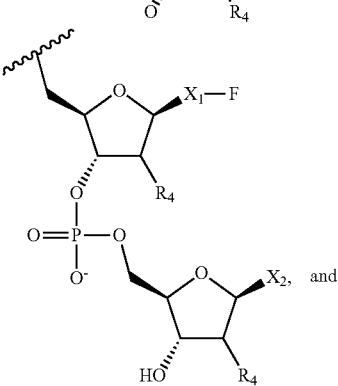

wherein $B_2$ is chosen from adenine, cytosine, guanine, thymine, uracil, hypoxanthine, and 5-methylcytosine;

$X_1$ is chosen from methylene; $L_2$; a base which does not base pair with any of adenine, cytosine, guanine, thymine, and uracil; and group comprising $L_2$ and a base which does not base pair with any of adenine, cytosine, guanine, thymine, and uracil;

wherein $L_2$ is chosen from alkyl, alkenyl, alkynyl, aryl, heteroaryl, heterocyclyl, ester, amino, and sulfonyl;

$X_2$ is chosen from H, $CH_3$, and a base which does not base pair with any of adenine, cytosine, guanine, thymine, and uracil;

each $R_4$ is H, OH, halogen (including fluorine, chlorine, bromine, and iodine), alkyl (including $CH_3$, $CH_2CH_3$) or alkoxy (both substituted and unsubstituted) (including $OCH_3$ and $OCH_2CH_3$); and $Y_2$ is chosen from $O^-$, $S^-$, $BH_3^-$, and $CH_3$.

For example, $R_3$ may be chosen from:

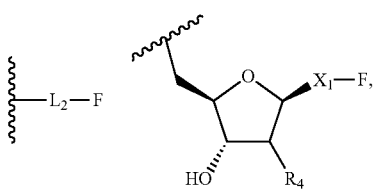

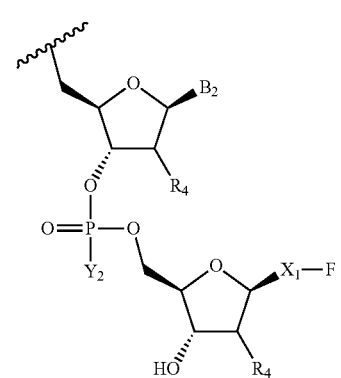

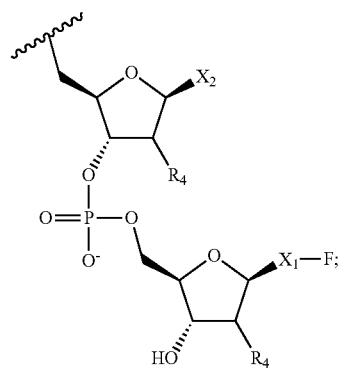

-continued

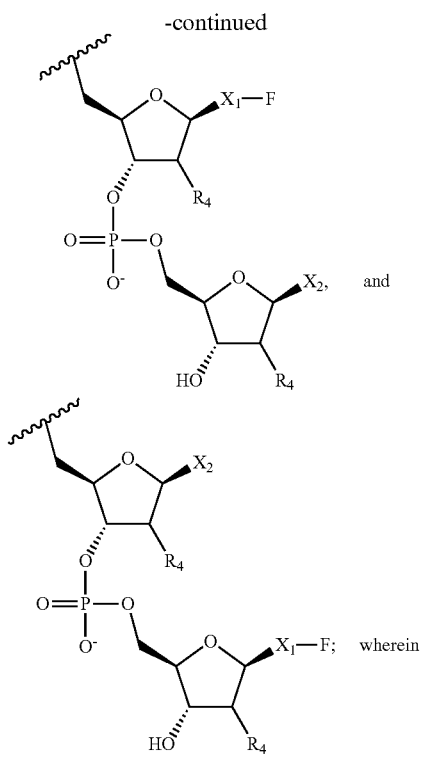

The bases $B_1$ and $B_2$ may each independently be, for example, a purine or a pyrimidine. For example, $B_1$ or $B_2$ may be an adenine, cytosine, guanine, thymine, uracil, or hypoxanthine. The bases $B_1$ and $B_2$ may also each be, for example, a naturally-occurring or synthetic derivative of a base, including pyrazolo(3,4-d)-pyrimidine; 5-methylcytosine (5-me-C); 5-hydroxymethyl cytosine; xanthine; hypoxanthine; 2-aminoadenine; 6-methyl or other alkyl derivative of adenine or guanine; 2-propyl or other alkyl derivative of adenine or guanine; 2-thiouracil; 2-thiothymine; 2-thiocytosine; 5-propynyl uracil; 5-propynyl cytosine; 6-azo uracil; 6-azo cytosine; 6-azo thymine; pseudouracil; 4-thiouracil; 8-halo (e.g., 8-bromo), 8-amino, 8-thiol, 8-thioalkyl, 8-hydroxyl and other 8-substituted adenine or guanine; 5-halo (e.g., 5-bromo), 5-trifluoromethyl and other 5-substituted uracil or cytosine; 7-methylguanine; 7-methyladenine; 8-azaguanine; 8-azaadenine; deazaguanine; 7-deazaguanine; 3-deazaguanine; deazaadenine; 7-deazaadenine; 3-deazaadenine; pyrazolo(3,4-d)pyrimidine; an imidazo(I,5-a)-1,3,5 triazinone; a 9-deazapurine; an imidazo(4,5-d)-pyrazine; a thiazolo(4,5-d)-pyrimidine; a pyrazin-2-one; a 1,2,4-triazine; a pyridazine; a 1,3,5 triazine; or the like.

Bases useful in the nucleotide analogs and methods described herein may permit a nucleotide analog which comprises a base $B_1$ (and a base $B_2$ according to some embodiments) to be incorporated into a nascent chain by a polymerase and to form one or more base pairs with one or more bases on the template strand. The term "base pair" encompasses not only the standard AT, AU, or GC base pairs, but also base pairs formed between nucleotides and/or nucleotide analogs comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the base analog hypoxanthine and either adenine, cytosine or uracil, wherein two hydrogen bonds are formed in the base pairing.

The nucleotide analogs may comprise a group which is removed by the 3' to 5' exonuclease activity of a proofreading polymerase after the analog is incorporated into a nascent or growing strand in order for polymerization to continue. In some embodiments, nucleotide analogs for use in the present methods are mononucleotide analogs, wherein the analogs comprise a label moiety in group $R_3$. Where desired, the label moiety comprises a photo-detectable label, or a photo-detectable label and a linker connecting the photo-detectable label to the 3' phosphate. For example, the linker is $L_2$ as defined herein. In such embodiments, after the analog is incorporated into a growing strand by a polymerase, the phosphate, optional linker, and photo-detectable label is removed to free the 3'-OH for linkage with a 5' phosphate of an incoming nucleotide analog in a subsequent incorporation step. This removal may be catalyzed by the proofreading 3' to 5' exonuclease activity of the proofreading enzyme.

In some embodiments, nucleotide analogs for use in the present methods are mononucleotide analogs, wherein the analogs comprise as a label moiety a group $R_3$ which comprises a photo-detectable label or a photo-detectable label and a linker connecting the photo-detectable label to the 3' phosphate, but wherein the linker cannot be cleaved to separate the photo-detectable label from the 3' phosphate. For example, the linker is $L_2$ as defined herein.

In some embodiments, nucleotide analogs having the structure of Formula I are binucleotide analogs, wherein the analogs comprise as a label moiety a group $R_3$ having the structure

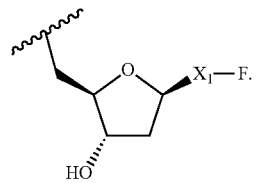

In some embodiments, nucleotide analogs having the structure of Formula I are trinucleotide analogs, wherein the analogs comprise as a label moiety group $R_3$ having the structure of:

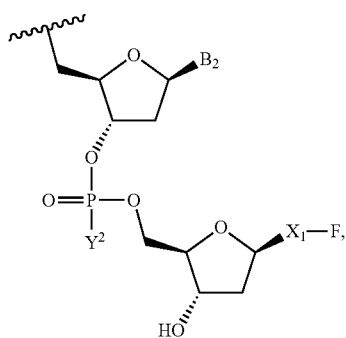

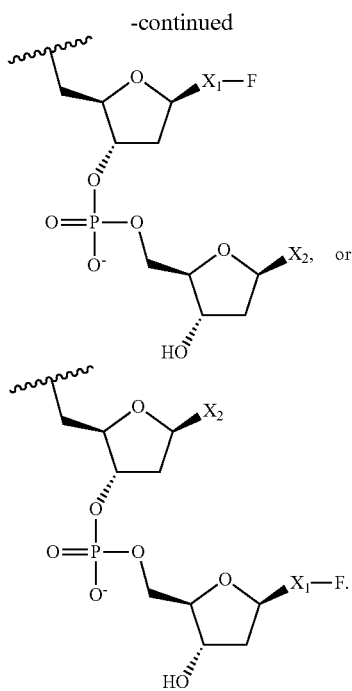

In such binucleotide or trinucleotide embodiments, F is a photo-detectable label, $Y_2$ is O, $CH_3$, $BH_2$ or S, and each of groups $X_1$ and $X_2$ is a group which is not able to base pair with a corresponding base in a template strand. In some embodiments, group $X_1$ is a linker. Suitable linkers include, for example, alkyl, alkenyl, alkynyl, aryl, heteroaryl, heterocyclyl, ester, amino, sulfonyl linkers, or the like. In some embodiments, the linker is a substituted alkyl, alkenyl, alkynyl, or amino. In some embodiments, the linker is alkyl, alkenyl, alkynyl, or amino interrupted with heteroatoms. In some embodiments, for example, the linker is polyethylene glycol. The linker may be any suitable linker which is nonreactive and which minimizes steric hindrance between the photo-detectable label and the remainder of the nucleotide analog. In some embodiments, either or both of groups $X_1$ and $X_2$ is a base, including a naturally-occurring or synthetic pyrimidine or purine derivative, which is not complementary to any base pair in a target nucleic acid strand. In some embodiments, $X_2$ is an alkyl, alkenyl, alkynyl, aryl, heteroaryl, heterocyclyl, ester, amino, or sulfonyl group. In some embodiments, $X_2$ is hydrogen. In embodiments in which the analog is a trinucleotide analog comprising a base $B_2$ and group $Y_2$, $Y_2$ may be $S^-$, $CH_3$, or $BH_3^-$, whereby processive 3' to 5' excision of the nucleotide residue comprising base $B_2$ may be prevented following incorporation of the trinucleotide analog into a growing strand.

Each $R_4$ may be independently H, OH, halogen (including fluorine, chlorine, bromine, and iodine), alkyl (including $CH_3$, $CH_2CH_3$) or alkoxy (both substituted and unsubstituted) (including $OCH_3$ and $OCH_2CH_3$). In another embodiment, $R_4$ is independently H, OH, fluorine, or $OCH_3$. For example, all $R_4$ groups may be H. Alternatively, all $R_4$ groups may be OH.

The photo-detectable label F may be any moiety which can be attached to or associated with a nucleotide analog and which functions to provide a detectable signal. In some embodiments, the label is a fluorescent label, such as a small molecule fluorescent label. Useful fluorescent molecules (fluorophores) suitable as a fluorescent label include, but are not limited to: 1,5 IAEDANS; 1,8-ANS; 4-Methylumbelliferone; 5-carboxy-2,7-dichlorofluorescein; 5-Carboxyfluorescein (5-FAM); fluorescein amidite (FAM); 5-Carboxynapthofluorescein; tetrachloro-6-carboxyfluorescein (TET); hexachloro-6-carboxyfluorescein (HEX); 2,7-dimethoxy-4,5-dichloro-6-carboxyfluorescein (JOE); VIC®; NED™; tetramethylrhodamine (TMR); 5-Carboxytetramethylrhodamine (5-TAMRA); 5-HAT (Hydroxy Tryptamine); 5-Hydroxy Tryptamine (HAT); 5-ROX (carboxy-X-rhodamine); 6-Carboxyrhodamine 6G; 6-JOE; Light Cycler® red 610; Light Cycler® red 640; Light Cycler® red 670; Light Cycler® red 705; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; AFPs-AutoFluorescent Protein-(Quantum Biotechnologies); Texas Red; Texas Red-X conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (Tetramethyl-Rodamine-IsoThioCyanate); True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; interchelating dyes such as YOYO-3, Sybr Green, Thiazole orange; members of the Alexa Fluor® dye series (from Molecular Probes/Invitrogen) which cover a broad spectrum and match the principal output wavelengths of common excitation sources such as Alexa Fluor 350, Alexa Fluor 405, 430, 488, 500, 514, 532, 546, 555, 568, 594, 610, 633, 635, 647, 660, 680, 700, and 750; members of the Cy Dye fluorophore series (GE Healthcare), also covering a wide spectrum such as Cy3, Cy3B, Cy3.5, Cy5, Cy5.5, Cy7; members of the Oyster® dye fluorophores (Denovo Biolabels) such as Oyster-500, -550, -556, 645, 650, 656; members of the DY-Labels series (Dyomics), for example, with maxima of absorption that range from 418 nm (DY-415) to 844 nm (DY-831) such as DY-415, -495, -505, -547, -548, -549, -550, -554, -555, -556, -560, -590, -610, -615, -630, -631, -632, -633, -634, -635, -636, -647, -648, -649, -650, -651, -652, -675, -676, -677, -680, -681, -682, -700, -701, -730, -731, -732, -734, -750, -751, -752, -776, -780, -781, -782, -831, -480XL, -481XL, -485XL, -510XL, -520XL, -521XL; members of the ATTO series of fluorescent labels (ATTO-TEC GmbH) such as ATTO 390, 425, 465, 488, 495, 520, 532, 550, 565, 590, 594, 610, 611X, 620, 633, 635, 637, 647, 647N, 655, 680, 700, 725, 740; members of the CAL Fluor® series or Quasar® series of dyes (Biosearch Technologies) such as CAL Fluor® Gold 540, CAL Fluor® Orange 560, Quasar® 570, CAL Fluor® Red 590, CAL Fluor® Red 610, CAL Fluor® Red 635, Quasar® 570, and Quasar® 670.

In some embodiments, the photo-detectable label F interacts with a second photo-detectable moiety to modify the detectable signal provided by the first or second label, e.g., via Fluorescence resonance energy transfer ("FRET"; also known as Förster resonance energy transfer). In some embodiments, nucleotides incorporated into a nascent strand are detected using fluorescence resonance energy transfer (FRET)-based detection. For example, in some embodiments, a FRET-based method as described in U.S. Patent Application No. 2010/0035268 can be used. In such embodiments, a Quantum dot capable of acting as a fluorescence donor may be linked to a sequencing primer, and the nucleotide analogs used to synthesize the growing strand carry a label F which is a fluorescence acceptor. Incorporation of the fluorophore-labeled nucleotide analog into the growing nucleotide strand at a nucleic acid polymerizing enzyme reaction site is detected in real-time by detecting emission of the analog-linked fluorescence acceptor following fluorescence resonance energy transfer from the excited Quantum dot fluorescence donor. The identity of each incorporated nucleotide analog is determined by its fluorescent label, which is detectable while the analog is incorporated into the growing strand and until the noncomplementary moiety of the analog comprising the fluorescent label is removed by the 3' to 5' exonuclease activity of the proofreading polymerase.

In some embodiments, the nucleotide analog comprises a fluorescence quenching moiety Q. A fluorescence quenching moiety includes any moiety that is capable of absorbing the energy of an excited fluorescent label when located in close proximity to the fluorescent label and capable of dissipating that energy without the emission of visible light. Suitable fluorescence quenching moieties include, for example, Deep Dark Quencher I (DDQ-I); 4-((4-(dimethylamino)phenyl) azo)benzoic acid, succinimidyl ester (DABCYL); Eclipse® dark quencher; Iowa Black® FQ; BHQ-1; QSY-7; BHQ-2; Deep Dark Quencher II (DDQ-II); Iowa Black® RQ; QSY-21; BHQ-3, and the like. A fluorescence quenching moiety Q may be linked to the gamma or beta phosphate of a nucleotide analog. A fluorescence quenching moiety may be connected via a linker $L_1$ to the gamma or beta phosphate of the nucleotide triphosphate analog. Suitable linkers include, for example, alkyl, alkenyl, alkynyl, aryl, heteroaryl, heterocycloalkyl, ester, amino, sulfonyl, polyethylene glycol (PEG) linkers, or the like. The linker may be any suitable linker which is nonreactive and which minimizes steric hindrance between the fluorescence quenching moiety and the remainder of the nucleotide analog.

The term "alkyl" as used herein refers to a saturated straight or branched hydrocarbon, such as a straight or branched group of 1-22, 1-8, or 1-6 carbon atoms, referred to herein as $(C_1-C_{22})$alkyl, $(C_1-C_8)$alkyl, and $(C_1-C_6)$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkenyl" as used herein refers to an unsaturated straight or branched hydrocarbon having at least one carbon-carbon double bond, such as a straight or branched group of 2-22, 2-8, or 2-6 carbon atoms, referred to herein as $(C_2-C_{22})$alkenyl, $(C_2-C_8)$alkenyl, and $(C_2-C_6)$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkynyl" as used herein refers to an unsaturated straight or branched hydrocarbon having at least one carbon-carbon triple bond, such as a straight or branched group of 2-22, 2-8, or 2-6 carbon atoms, referred to herein as $(C_2-C_{22})$alkynyl, $(C_2-C_8)$alkynyl, and $(C_2-C_6)$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "aryl" as used herein refers to a mono-, bi-, or other multi-carbocyclic, aromatic ring system. The aryl group can optionally be fused to one or more rings selected from aryls, cycloalkyls, and heterocyclyls. The aryl groups can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl."

The term "heteroaryl" as used herein refers to a mono-, bi-, or multi-cyclic, aromatic ring system containing one or more heteroatoms, for example one to three heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2 to 5 carbon atoms and 1 to 3 heteroatoms, referred to herein as "$(C_2-C_5)$heteroaryl."

The term "heterocyclyl" or "heterocycle" as used herein refer to a saturated or unsaturated 3-, 4-, 5-, 6- or 7-membered ring containing one, two, or three heteroatoms independently selected from nitrogen, oxygen, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The term "ester" refers to the structure —C(O)O—, —C(O)O—$R_j$—, —$R_k$C(O)O—$R_j$—, or —$R_k$C(O)O—, where O is not bound to hydrogen, and $R_j$ and $R_k$ can independently be selected from alkoxy, aryloxy, alkyl, alkenyl, alkynyl, amide, amino, aryl, arylalkyl, cycloalkyl, ether, haloalkyl, heteroaryl, heterocyclyl. $R_k$ can be a hydrogen, but $R_j$ cannot be hydrogen. The ester may be cyclic, for example the carbon atom and $R_j$, the oxygen atom and $R_k$, or $R_j$ and $R_k$ may be joined to form a 3- to 12-membered ring. Exemplary esters include, but are not limited to, alkyl esters wherein at least one of $R_j$ or $R_k$ is alkyl, such as —O—C(O)-alkyl-, —C(O)—O-alkyl, -alkyl-C(O)—O-alkyl-, etc. Exemplary esters also include aryl or heteroaryl esters, e.g. wherein at least one of $R_j$ or $R_k$ is a heteroaryl group such as pyridine, pyridazine, pyrimidine and pyrazine, such as a nicotinate ester. Exemplary esters also include reverse esters having the structure —$R_k$C(O)O—, where the oxygen is bound to the parent molecular group. Exemplary reverse esters include succinate, D-argininate, L-argininate, L-lysinate and D-lysinate. Esters also include carboxylic acid anhydrides and acid halides.

The term "amino" as used herein refers to the form —$NR_dR_e$ or —$N(R_d)R_e$— where $R_d$ and $R_e$ are independently selected from alkyl, alkenyl, alkynyl, aryl, arylalkyl, carbamate, cycloalkyl, haloalkyl, heteroaryl, heterocyclyl, and hydrogen. The amino can be attached to the parent molecular group through the nitrogen. The amino also may be cyclic, for example, $R_d$ and $R_e$ may be joined together or with the N to form a 3- to 12-membered ring, e.g., morpholino or piperidinyl. The term amino also includes the corresponding quaternary ammonium salt of any amino group. Exemplary amino groups include alkyl amino groups, wherein at least one of $R_d$ and $R_e$ is an alkyl group.

The term "sulfonyl" as used herein refers to the structure $R_uSO_2$—, where $R_u$ can be alkyl, alkenyl, alkynyl, aryl, cycloalkyl, and heterocyclyl, e.g., alkylsulfonyl. The term "alkylsulfonyl" as used herein refers to an alkyl group attached to a sulfonyl group. "Alkylsulfonyl" groups can optionally contain alkenyl or alkynyl groups.

"Alkyl," "alkenyl," "alkynyl," and "amino" groups can be substituted with or interrupted by or branched with at least one group selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, thioketone, ureido, and nitrogen. The substituents may be branched to form a substituted or unsubstituted heterocycle or cycloalkyl. The linker may be an alkyl optionally interrupted with one or more heteroatoms, such as oxygen. In some embodiments, the linker is polyethyleneglycol (PEG).

As used herein, a "suitable substituent" refers to a group that does not nullify the synthetic or enzymatic utility of the nucleotide analogs or the intermediates useful for preparing them. Examples of suitable substituents include, but are not limited to: $C_{1-22}$, $C_{1-8}$, and $C_{1-6}$ alkyl, alkenyl or alkynyl; $C_{1-6}$ aryl, $C_{2-5}$ heteroaryl; $C_{3-7}$ cycloalkyl; $C_{1-22}$, $C_{1-8}$, and $C_{1-6}$ alkoxy; $C_6$ aryloxy; —CN; —OH; oxo; halo, carboxy; amino, such as —NH($C_{1-22}$, $C_{1-8}$, or $C_{1-6}$ alkyl), —N($C_{1-22}$, $C_{1-8}$, and $C_{1-6}$ alkyl)$_2$, —NH(($C_6$)aryl), or —N(($C_6$)aryl)$_2$; formyl; ketones, such as —CO($C_{1-22}$, $C_{1-8}$, and $C_{1-6}$ alkyl), —CO(($C_6$ aryl) esters, such as —$CO_2$($C_{1-22}$, $C_{1-8}$, and $C_{1-6}$ alkyl) and —$CO_2$ ($C_6$ aryl). One of skill in the art can readily choose a suitable substituent based on the stability and biochemical and synthetic activity of the nucleotide analogs.

The term "acceptable salt(s)" refers to salts of acidic or basic groups that may be present in compounds used in the present compositions. Acceptable salts include salts which will not interfere with the reactions contemplated herein and are not otherwise undesirable. Acceptable salts do not differ in activity from their free base, and may include salts commonly referred to as pharmaceutically acceptable salts, which are non-toxic salts that retain the biological activity of the free base. Compounds included in the present compositions that are acidic in nature are capable of forming base salts with various cations. Examples of such salts include alkali metal or alkaline earth metal salts, including, for example, calcium, magnesium, sodium, lithium, and potassium salts. Acceptable salts may also include zinc, iron, ammonium, copper, manganese, aluminum salts and the like. Acceptable salts may also be those derived from organic non-toxic bases, and may include salts of primary, secondary, and tertiary amines, substituted amines, including naturally occurring substituted amines, cyclic amines and basic ion exchange resins, such as isopropylamine, tripropylamine, ethanolamine, 2-diethylaminoethanol, 2-dimethylaminoethanol, dicyclohexylamine, lysine, glutamine, arginine, histidine, caffeine, procain, hydrabamine, choline, betaine, ethylenediamine, glucosamine, methylglucamine, theobromine, purines, piperazines, piperidine, polyamine resins and the like. In addition, salts may be formed from acid addition of certain organic and inorganic acids with basic centers of the purine, specifically guanine, or pyrimidine base. Finally, embodiments of the compounds described herein include their un-ionized as well as zwitterionic form and/or hydrate or solvate forms.

Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quenching group, its absorption spectrum must overlap the emission spectrum of the fluorophore (Stryer, L., ANN. REV. BIOCHEM. 47: 819-846 (1978); C. R. Cantor and P. R. Schimmel, "Biophysical Chemistry—part II: Techniques for the Study of Biological Structure and Function," W. H. Freeman and Co., San Francisco, U.S.A., 1980 (pages 448-455); and Selvin, P. R., METHODS IN ENZYMOLOGY, 246: 300-335 (1995)). Efficient FRET interaction requires that the absorption and emission spectra of the pair have a large degree of overlap. The efficiency of FRET interaction is linearly proportional to that overlap. (See Haugland, R. P., et al. PROC. NATL. ACAD. SCI. USA, 63: 24-30 (1969)). Typically, a large magnitude of signal (i.e., a high degree of overlap) is required. FRET pairs, including fluorophore-quenching group pairs, are therefore typically chosen on that basis.

Practical guidance is readily available in the literature for selecting appropriate FRET donor-acceptor pairs for particular probes, as exemplified by the following references: Pesce et al., Eds., "Fluorescence Spectroscopy," Marcel Dekker, New York, 1971; White et al., "Fluorescence Analysis: A Practical Approach," Marcel Dekker, New York, 1970. The literature also includes references providing exhaustive lists of fluorescent and chromogenic molecules and their relevant optical properties for choosing reporter-quencher pairs (see, for example, Beriman, HANDBOOK OF FLUORESCENCE SPECTRA OF AROMATIC MOLECULES, 2ND EDITION, Academic Press, New York, 1971; Griffiths, COLOUR AND CONSTITUTION OF ORGANIC MOLECULES, Academic Press, New York, 1976; Bishop, Ed., INDICATORS, Pergamon Press, Oxford, 1972; Haugland, HANDBOOK OF FLUORESCENT PROBES AND RESEARCH CHEMICALS, Molecular Probes, Eugene, 1992; Pringsheim, FLUORESCENCE AND PHOSPHORESCENCE, Interscience Publishers, New York, 1949. Further, the literature provides ample guidance for derivatizing reporter and quencher molecules for covalent attachment via common reactive groups that can be added to a nucleotide analog (see, e.g., Haugland (supra); U.S. Pat. Nos. 3,996,345 and 4,351,760).

In some embodiments, the nucleotide analogs each comprise a base-pairing moiety at their 5' end which comprises a nucleotide analog which comprises a base that is able to base pair with a corresponding base of the target nucleic acid in a reaction site of the reaction complex. Upon incorporation of the nucleotide analog into the nascent strand, the identity of the first base of the incorporated nucleotide analog may be determined by detection of the corresponding photo-detectable label in the label moiety.

In some embodiments, the nucleotide analogs each comprise a base—pairing moiety at their 5' end which comprises two nucleotide residues, each of which comprises a base that is able to base pair with corresponding bases of the target nucleic acid in a reaction site of the reaction complex. Upon incorporation of the nucleotide analog into the nascent strand, the identity of the first two bases of the incorporated nucleotide analog may be determined by detection of the corresponding photo-detectable label in the label moiety.

In some embodiments, the nucleotide analogs each comprise a base-pairing moiety at their 5' end which comprises three nucleotide residues at their 5' end, each of which comprises a base that is able to base pair with a corresponding base of the target nucleic acid in a reaction site of the reaction complex. Upon incorporation of the nucleotide analog into the nascent primer strand, the identity of the first three bases of the incorporated nucleotide analog may be determined by detection of the corresponding photo-detectable label in the label moiety.

The number of types of nucleotide analogs used in the methods described herein may be $4^N$ types of nucleotide analogs, wherein N is the number of nucleotide residues in the base-pairing moiety at the 5' end of each analog which are able to base pair with a corresponding base of the target nucleic acid. For example, the analogs may be mononucleotides which each contain one base $B_1$ that is able to base pair with a corresponding base of the target nucleic acid (see, e.g. Example 5, infra, and Formula VI). Where a plurality of types of mononucleotides are used in a sequencing reaction, the number N of complementary bases $B_1$ is one, thus a template nucleic acid, together with a polymerase and a sequencing primer, is contacted with $4^1$, or four types of mononucleotide analogs, wherein each type contains one of the four bases adenine, cytosine, thymine (or uracil), and guanine as base $B_1$. Where desired, each of the four types of analogs can comprise a unique fluorescent label F corresponding to the identity of the base $B_1$.

In some embodiments, the analogs are binucleotides, wherein a base-pairing moiety at the 5' end of the analog is a nucleotide residue having a complementary base $B_1$, and wherein a label moiety connected to the 3' position of the base-pairing moiety is a nucleotide residue comprising a noncomplementary group $X_1$ and a fluorescent label F, as described herein (see, e.g. Example 1, infra, and Formula II). According to such embodiments, the number N of complementary bases $B_1$ is one, thus a target nucleic acid, together with a polymerase and a sequencing primer, is contacted with $4^1$, or four types of binucleotide analogs, wherein each type contains one of the four bases adenine, cytosine, thymine, and guanine as base $B_1$. Where desired, each of the four types of analogs comprises a unique fluorescent label F corresponding to the identity of the base $B_1$.

In some embodiments, the nucleotide analog is a trinucleotide analog, wherein a base-pairing moiety at the 5' end of the analog comprises two nucleotide residues having complementary bases $B_1$ and $B_2$, respectively, and wherein a label moiety connected to the 3' position of the base-pairing moiety is a nucleotide residue comprising a non-complementary group $X_1$ and a fluorescent label F, as described herein (see, e.g. Example 9, infra, and Formula X). According to such embodiments, the number N of complementary bases $B_1$ and $B_2$ is two, thus a target nucleic acid, together with a proofreading polymerase and a sequencing primer, is contacted with $4^2$, or sixteen types of binucleotide analogs. Where desired, each type contains one of the sixteen combinations of two sequential bases of adenine, cytosine, thymine, or guanine as bases $B_1$ and $B_2$, and wherein each of the sixteen types of analogs comprises a unique fluorescent label F corresponding to the sequential combination of bases $B_1$ and $B_2$.

1.5 Preparation of Analogs

Base-linked and phosphate-linked fluorophores and quenchers are well known in the art. They can be obtained, for example, from Life Technologies (San Diego, Calif.), Sigma-Genosys (The Woodlands, Tex.), AnaSpec (Fremont, Calif.), Eurofins MWG Operon (Huntsville, Ala.), Glen Research (Sterling, Va.) or Integrated DNA Technologies (Coralville, Iowa). Examples of base-linked fluorophores include, but are not limited to, modified thymidine or uracil bases where the fluorophore is attached, for example, at the 5-position of a uracil group. Linkers of various lengths may be used to attach the fluorophore to the base.

In some cases, base-linked fluorophores are incorporated into the nucleotide analogs by post-synthesis modification of nucleotide analogs that were synthesized with reactive groups linked to a noncomplementary base. Such reactive groups include, but are not limited to, amino groups (which can react, for example, with an activated carboxylic acid or a N-hydroxysuccinimide); azide or alkyne groups (which can react with an alkyne or azide, respectively, in a "click" triazole-forming reaction); or aldehydes (which may react with amino groups to form a Schiff's base, with hydrazino groups to form hydrazones, and with semicarbazides to form semi-carbazones).

The concentration of nucleotide analogs in a sequencing reaction mixture may be any suitable concentration that produces an appropriate interpulse duration. An "interpulse duration" refers to the time between successive signals detected from a labeled nucleotide analog associating with and becoming incorporated into a growing strand in the incorporation site of a polymerase. While nucleotide concentrations for nucleic acid amplification by PCR are typically about 200 micromolar, and while concentrations for cycle-sequencing are about 400 micromolar, the concentration of labeled nucleotides employed in single-molecule sequencing is typically much lower, for example about 250 nM. In some embodiments, the concentration of nucleotide analogs used in a sequencing reaction is from about 50 nM to 10 micromolar. In some embodiments, the concentration of nucleotide analogs is less than 50 nM, or greater than 10 micromolar. In some embodiments, the concentration of nucleotide analogs is from about 50 nM to about 500 nM, from about 75 nM to about 400 nM, from about 100 nM to about 300 nM, or from about 125 nM to about 250 nM. In some embodiments, the concentration of nucleotide analogs is about 250 nM. In some embodiments, the interpulse duration is from about 0.2 seconds to 1 second. In some embodiments, the interpulse duration is less than 0.2 seconds, or more than 1 second. In some embodiments, the interpulse duration is from about 0.2 seconds to 0.6 seconds. In some embodiments, the interpulse duration is from about 0.3 seconds to 0.5 seconds.

In some embodiments, sequencing is performed using four types of nucleotide analogs disclosed herein, each type comprising a distinct base (adenine, cytosine, guanine, thymine/uracil) distinguishable by its unique detectable label. The temporal order or time sequence of the four unique labels detectable from the incorporation site is indicative of the sequences of one or more types of bases incorporated into the nascent strand, and hence allowing the deduction of the nucleic acid sequence of the template having the sequence of a target molecule.

In some embodiments, the subject sequencing procedure is performed using less than four labels. For example, sequencing is performed using three types of mononcleotide or binucleotide analogues disclosed herein, each type comprising a distinct base distinguishable by its unique detectable label, and a fourth type of nucleotide analog comprising no detectable label. The sequence can then be determined by detecting the three labels, with the fourth nucleotide being detectable as a long delay between observing two labeled nucleotide analogs.

The subject sequencing method can also be performed with two types of mono- or bi-nucleotide analogues disclosed herein, each type comprising a distinct base distinguishable by its unique detectable label, and a third and a fourth type of nucleotide analog comprising no detectable label. The sequence of the template and hence the target nucleic acid can be deduced by sequencing the template strand and its complement. Alternatively, the template strand may be sequenced at least twice with different pairs of labeled binucleotide analogs (e.g., the first pair of labeled binucleotides comprising pyrimidines C and T, and the second pair of labeled binucleotides comprising purines A and G, or with any other possible pairing permutations amongst A, T, C and G containing nucleotides). Another variation is to use sets of mono- or bi-nucleotide analogs wherein two types of the nucleotide analogs comprise one kind of detectable label while the other two types of the nucleotide analogs comprise a second kind of detectable label. Further description of sequencing methods utilizing two detectable labels can be found in Sauer et al., "Detection and Identification of Single Dye Labelled Mononucleotide Molecules Released From an Optical Fiber in a Microcapillary: First Steps Towards a New Single Molecule DNA Sequencing Technique," PHYS. CHEM. CHEM. PHYS. 1:2471-77 (1999).

The subject sequencing method can be performed using one type of mono- or bi-nucleotide analog being labeled with a first detectable label, and the other three types of mono- or bi-nucleotide analogs being labeled with a second detectable label. The sequence is deduced by sequencing the template molecule at least three times, each time with a different nucleotide analog comprising a unique detectable label. It should be noted that an equivalent method may utilize three types of mono- or bi-nucleotide analogs that each comprise the same detectable label and a fourth binucleotide analog that comprises no detectable label.

In some related but distinct embodiments, sequencing is performed using the trinucleotide analogs described herein, where each trinucleotide analog comprises two nucleotides that may base pair with a template molecule, such that each trinucleotide analog is complementary to a different dinucleotide sequence. As such, there are sixteen types of possible trinucleotide analogs. In some embodiments of the invention, sixteen different detectable labels are used to distinguish amongst the trinucleotide analogs. In some embodiments, the labels may be detectable by different means. For fluorescently labeled trinucleotide analogs, it is possible to distinguish the labels not only be emission wavelength, but also other parameters, including but not limited to fluorescence lifetime and fluorescence intensity.

In some embodiments, sequencing may be performed using less than 16 detectable labels. It is well known in the art that the interactions of a fluorophore and its surrounding molecular environment (e.g. nearby bases) can affect the fluorophore's characteristics. For example, coumarin-dGTP has a shorter fluorescence lifetime than coumarin-CTP. As a result, multiple trinucleotide analogs may be distinguishable using the same fluorescent label.

In other embodiments, some trinucleotide analogs may comprise the same detectable label and/or some trinucleotide analogs may comprise no detectable label. The sequence may then be determined by resequencing the template molecule multiple times with different combinations of trinucleotide analogs and detectable labels. For example, a first sequencing cycle may be performed with a set of trinucleotide analogs wherein the analogs comprise two bases complementary to a template, e.g., adenine as the 5' base-pairing unit (A̲A, A̲C, A̲G, or A̲T, collectively as A-subset), cytosine as the 5' base-pairing nucleotide (C̲A, C̲C, C̲G, or C̲T, collectively as C-subset), guanine as the 5' base-pairing nucleotide (G̲A, G̲C, G̲G, or G̲T, collective as G-subset), and thymine as the 5' base-pairing nucleotide (T̲A, T̲C, T̲G, or T̲T, collectively as T-subset) These subsets of the trinucleotides each carry a distinct label, such as Alexa Fluor 405 for the A-subset, Alexa Fluor 488 for the C-subset, Alexa Fluor 546 for the G-subset, and Alexa Fluor 635 for the T-subset. Sequencing performed with this set of trinucleotide analogs would thus determine the identity of every second base of the template strand. A second sequencing cycle may then be performed using a second set of labeled trinucleotide analogs wherein the analogs comprising adenine as the second, downstream base-pairing unit (that is, wherein the analogs comprise the sequence AA̲, CA̲, GA̲, or TA̲), cytosine as the downstream base-pairing unit (AC̲, CC̲, GC̲, or TC̲), guanine as the downstream base-pairing nucleotide (AG̲, CG̲, GG̲, or TG̲), and thymine as the downstream base-pairing nucleotide (AT̲, CT̲, GT̲, or TT̲). Like the first set, each subset in the second round of sequencing carries a distinct label. A second sequencing cycle performed with this second set of trinucleotide analogs would reveal the identity of the rest of the template strand, thus determining the complete sequence of the template. Another possible scheme for the second sequencing cycle is to employ the same set of trinucleotide analogs as the first sequencing cycle, but with a primer differing in length from the primer used in the first sequencing cycle by an odd number of nucleotides, including but not limited to 7 nucleotides shorter, 5 nucleotides shorter, 3 nucleotides shorter, 1 nucleotide shorter, 1 nucleotide longer, 3 nucleotides longer, 5 nucleotides longer, 7 nucleotides longer. In this scheme, a primer that only differs in length by an odd number of nucleotides permits identifying the second base in the template strand whose identity is not revealed during the first round of sequencing reaction. Embodied in the present invention are other alternative schemes involving varying the set of labeled trinucleotide analogs, utilizing more or fewer sequencing cycles, and/or utilizing various combinations of detectable labels.

For single-molecule sequencing by synthesis, the present methods can offer the advantage of being able to resequence single molecules. For example, a template nucleic acid molecule to be sequenced can be provided in circular form together with a sequencing primer. Resequencing can be achieved by performing a plurality of sequencing cycles such that a sequence read is obtained that is greater than the number of nucleotides in the template nucleic acid molecule. The sequencing read therefore comprises information that redundantly identifies the base in at least one position in the template nucleic acid molecule. In some embodiments, the sequencing read comprises information that redundantly identifies at least 25%, 50%, 75%, 90%, 91%, 92%, 93%, 94%, 95%, 96%, 97%, 98%, 99%, or 100% of the bases in the template nucleic acid molecule. In some embodiments, the sequencing read comprises information that identifies at least 25%, 50%, 75%, 90%, 91%, 92%, 93%, 94%, 95%, 96%, 97%, 98%, 99%, or 100% of the bases in the template nucleic acid molecule with two-fold, three-fold, four-fold, five-fold, seven-fold, or ten-fold or greater redundancy. By resequencing the same molecule, sequencing errors are expected to fall as the power of the number of sequencing reads. For example, if per-base error rates for a single read are $10^{-3}$, then after three reads, this falls to $(10^{-3})^3$, i.e., $10^{-9}$. This is particularly advantageous for single-molecule sequencing in the event that nucleotide analogs used for sequencing lose their labels, resulting in, e.g., spurious deletions.

Where desired, the polymerase enzyme or enzyme complex can be replaced with a different enzyme set during the nucleic acid polymerization reaction. Similarly, reagents including nucleotide analogs and buffers can also be replaced or replenished during the nucleic acid polymerization reaction.

1.6 Additional Applications

In some embodiments, fluorescently labeled nucleotide analogs may act as acceptor chromophores for a donor chromophore attached to a polymerase. Accordingly, in these embodiments, the donor chromophore located on the polymerase may excite an acceptor chromophore on a growing nucleic acid strand replicated from the target nucleic acid. Fluorescently labeled nucleotide analogs not proximate to the polymerase may be not excited due to the rapid falloff in FRET efficiency. In some embodiments the donor molecule may be, e.g., another fluorophore, e.g., a quantum dot. Quantum dots, e.g., semiconductor quantum dots are known in the art and are described in, e.g., International Publication No. WO 03/003015. Means of coupling quantum dots to, e.g., biomolecules are known in the art, as reviewed in, e.g., Mednitz et al., NATURE MATERIALS 4:235-46 (2005) and U.S. Patent Publication Nos. 2006/0068506 and 2008/0087843, published Mar. 30, 2006 and Apr. 17, 2008, respectively. In some embodiments, quantum dots may be conjugated to a DNA polymerase molecule. The skilled artisan will appreciate that when conjugating fluorophores to, e.g., a DNA polymerase, care must be taken to retain enzyme function by mitigating any effect of conjugating the fluorophore on the primary, secondary, and tertiary structures of the enzyme.

1.7 Multi Photon Excitation

In some embodiments, a fluorophore may be excited by two or more photons. For example, in some embodiments, excitation of either a donor or acceptor fluorophore in FRET may be via two or more photons. Two photon and multi-photon excitation are described further in, e.g., U.S. Pat. Nos. 6,344,653 and 5,034,613.

1.8 Target Sequences

Target sequences comprise the sequence to be determined by the present methods. The subject invention can be utilized to sequence a wide variety of target nucleic acids. Target sequences may comprise a completely unknown sequence (e.g., de novo sequencing), a partially unknown sequence (e.g., for SNP identification), or may be fully known (e.g., to confirm the presence of a transcribed product or to identify alternate splice sites). In some embodiments, the target sequences may contain known sequences repeated an unknown number of times, such as may be used in DNA fingerprinting, telomere analysis, and/or diagnosis of certain genetic disorders. Target sequences may include ribonucleic acid (RNA) and/or deoxyribonucleic acid (DNA), including but not limited to modified versions of such nucleic acids, such as CpG methylation for bisulfite sequencing.

Target sequences may be isolated from a biological sample containing other components, such as proteins, lipids, sugars, and non-target nucleic acids. Samples may be obtained from any cellular material, including but not limited to that obtained from an animal, plant, bacterium, fungus, and cell cultures. Samples may be obtained directly from tissue, body fluid specimens, or other samples, including but not limited to blood, lymph fluid, urine, cerebrospinal fluid, seminal fluid, saliva, sputum, and stool. Samples may also be obtained from tissues that have been infected with a virus or other intracellular pathogen, or from viral particles, samples, or preparations. Methods of producing samples and extracting nucleic acid sequences are well known in the art.

In some embodiments, the nucleic acids of the sample may be fragmented and otherwise modified to produce fragments of suitable length or composition to serve as target sequences for sequencing. Fragmentation and other modifications may be performed by any method known in the art, including but not limited to sonication, restriction enzyme digestion, ligation to another nucleic acid sequence, and covalent linkage to another molecule or solid support.

In some embodiments, target sequences may include non-natural sequences, such as parts of plasmids or artificially generated tags. Target sequences may be a mixture of sequences, including but not limited to total RNA extracted from a biological specimen, a cDNA library, or genomic DNA. Target sequences may be of any length, e.g., between 5 bases and 50 kb in length, between 5 bases and 20 kb in length.

In some embodiments, target sequences may compose all or part of a template strand, which is the strand that serves as the template for nucleic acid synthesis by the polymerase of this invention.

The template comprises at least a target sequence for amplification and optionally additional sequence(s), which may be utilized for primer hybridization, template immobilization, probe hybridization, other purposes, or left unused. The template may be of any shape, including but not limited to linear, circular, and supercoiled. The template may be single-stranded, double-stranded, double-stranded with single-stranded regions (e.g., in a hairpin loop), nicked, or modified (such as by methylation), and may contain RNA, DNA, or non-natural nucleotides. The template may be immobilized to a surface as described above for the polymerase or may be free in solution. Immobilization may occur at the 5' end, the 3' end, anywhere along the sequence, such as through hybridization to an immobilized, complementary oligonucleotide, or some combination thereof.

Target nucleic acids suitable for detection may include any nucleic acid, including, for example, DNA, RNA, or PNA (peptide nucleic acid), and may contain any sequence—both known and unknown, including naturally occurring or artificial sequences. The nucleic acid may be naturally derived, recombinantly produced, or chemically synthesized. The nucleic acid may comprise naturally-occurring nucleotides, nucleotide analogs not existing in nature, or modified nucleotides. The length of the nucleic acid to be detected may vary based on the actual application. In some embodiments, the nucleic acid may include at least 10, 20, 50, 100, 200, 500, 1000, 2000, 5000, 10000, 20000 bases, or more. In some embodiments, the nucleic acid may be from 10 to 20, from 10 to 50, from 10 to 100, from 50 to 100, from 50 to 500, from 50 to 1000, from 50 to 5000, from 500 to 2000, from 500 to 5000, from 1000 to 5000 bases, or from 5 bases to 20 kb, or from 5 bases to 50 kb.

A target nucleic acid may be single-stranded for detection. Single stranded nucleic acids may be derived from a double stranded molecule by means known in the art including, for example, heating or alkali or other chemical treatment. Single stranded nucleic acid templates may also be produced by, e.g., chemical or in vitro synthesis.

In some embodiments, the nucleic acid to be detected may be circular. In some embodiments, the methods comprise providing a circular nucleic acid molecule comprising an insert with a known sequence, which can be used as a binding site for a primer. The circular nucleic acid molecule can be provided in a single stranded state, a double stranded state, or a mix of both states, and will generally comprise at least one covalently closed strand. Double stranded circular molecules may comprise a nicked strand or a second covalently closed strand.

In some embodiments, the circular nucleic acid molecule is provided by isolating it in circular form from its source, if part of its sequence is known and thus can serve as the nucleic acid insert (e.g., a conserved motif within the sequence of a gene contained in the circular molecule may be known, or the molecule may be known to contain a sequence based on its ability to hybridize under high stringency conditions to another nucleic acid of known sequence). In some embodiments, the sequence of the nucleic acid insert is known only inexactly, as would be the case when knowledge of the sequence is derived from stringent hybridization properties. In some embodiments, the sequence of the nucleic acid insert is known exactly, such as would be the case when the circular nucleic acid molecule has a known backbone sequence or has been engineered to contain a known sequence.

In some embodiments, the circular nucleic acid molecule is provided by performing an in vitro reaction or reactions to incorporate a linear nucleic acid sample into a circular molecule along with a nucleic acid insert. The in vitro reaction or reactions can in some embodiments comprise ligation by a ligase and/or other strand joining reactions such as can be catalyzed by various enzymes, including recombinases and topoisomerases. DNA ligase or RNA ligase may be used to enzymatically join the two ends of a linear template, with or without an adapter molecule or linkers, to form a circle. For example, T4 RNA ligase couples single-stranded DNA or RNA, as described in Tessier et al., ANAL. BIOCHEM., 158: 171-78 (1986). CIRCLIGASE™ (Epicentre, Madison, Wis.) may also be used to catalyze the ligation of a single stranded nucleic acid. Alternatively, a double stranded ligase, such as *E. coli* or T4 DNA ligase, may be used to perform the circularization reaction.

In some embodiments, providing the circular nucleic acid molecule comprises replicating a nucleic acid template by extending from at least one primer (which can include random primers with 5' flaps of known sequence that can serve as the nucleic acid insert) comprising complementary regions and circularizing the amplified nucleic acid, such as may be catalyzed by a ligase or a recombinase; the amplified nucleic acid may in some embodiments be processed at its ends, e.g., by restriction or phosphorylation, prior to circularization.

In some embodiments, the circular nucleic acid molecule is provided by performing chemical circularization. Chemical methods employ known coupling agents such as BrCN plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. The ends of a linear template may also be joined by condensing a 5'-phosphate and a 3'-hydroxyl, or a 5'-hydroxyl and a 3'-phosphate.

In some embodiments, the circular nucleic acid molecule contains an insert sequence that could be considered an end link primer (discussed below) except that it is not at an end, since the molecule is circular.

In some embodiments, the target nucleic acid comprises one or more sequence repeats. A "sequence repeat" refers to a stretch of at least 3 consecutive nucleotide bases of the same types, or a stretch of at least 3 consecutive nucleotide bases which is repeated at least once in a given target nucleic acid. For example, a sequence repeat can be a stretch of A-containing nucleotides (e.g., $(A)n$), T-containing nucleotides (e.g., $(T)n$), C-containing nucleotides (e.g., $(C)n$), or G-containing nucleotides (e.g., $(G)n$), wherein n is an integer of 3, 4, 5, 6, 7, 8, 9, 10, or greater. In some instance, n is an integer between 3 to 10, between 3 to 300, between 3 to 15, 3 to 30, 3 to 150.

2. Detection Systems

The practice of the sequencing methods disclosed herein typically involves the use of a detector to detect the signals from a nucleotide analog being incorporated by the polymerase enzyme or enzyme complex in a template dependent manner. Such detection can be carried out to register the temporal order of the signals corresponding to the consecutive incorporation events while the nucleic acid polymerization reaction is taking place.

Any suitable detector or system thereof will provide a detection site encompassing the reaction complex that comprises a polymerase enzyme or enzyme complex, and a template. The time between the initial detection of the label moiety in the detection site and its removal from the detection site is the "detection duration." The length of the detection duration may vary, for example, with the reaction conditions, the polymerase used, and the nucleotide analog, and is also subject to stochastic variations in single enzyme kinetics. In some embodiments, the nucleotide analog utilized in the present invention provide a prolonged detection duration as compared to a labeled nucleotide analog whose label is removed via the 5' to 3' polymerization activity of the enzyme or enzyme complex. For example, the detection duration can be prolonged by at least 1, 5, 10, 20, 50, 100, 200, 500, 1000 times or even higher. In some aspects, the detection duration lasts from about 30 milliseconds to about 300 milliseconds, or from about 50 milliseconds to about 250 milliseconds. In some aspects, the detection duration may be no less than about 30, 40, 50, 60, 70, 80, 90, 100, 110, 120, 130, 140, 150, 160, 170, 180, 190, 200, 210, 220, 230, 240, 250, 260, 270, 280, 290, or 300 milliseconds. In some embodiments, two successive detecting steps (corresponding to the two consecutive incorporation events in a template dependent manner) on average are separated by e.g., about 0.2 to about 1 second, from about 0.2 to 0.6 seconds, or from about 0.3 to 0.5 seconds. In some embodiments, the methods of the invention may be performed under conditions whereby any two successive detecting steps are separated by at least about 0.2, 0.3, 0.4, 0.5, 0.6, 0.7, 0.8, 0.9, or 1 second.

Any detector or system thereof that is capable of providing single molecule detection may be utilized for this invention. The choice of detector or detector system will depend on the types of labels utilized in the nucleic acid polymerization reaction. Detectors may be configured to detect radioactivity, chemiluminesce, enzymatic activity, conductivity, charge, and/or fluorescence.

A wide variety of detection systems can be employed in practicing the sequencing methods disclosed herein. They include but are not limited to the detection systems described in U.S. patent application Ser. No. 13/046,457, filed Mar. 11, 2011, entitled "Single-Molecule Detection System and Methods". Briefly, a target nucleic acid to be sequenced using the methods described herein is localized on a movable light coupler as part of a nucleic acid synthesizing reaction complex. Such a system utilizes a zero-mode waveguide (ZMW) to facilitate single molecule detection by e.g., creating a defined excitation light field and using nano-scale wells to minimize reaction volumes, thereby greatly minimizing background signals. Suitable detection systems incorporating ZMW's for use with the methods described herein also include the systems described in U.S. patent application Ser. No. 12/801,503, filed Jun. 11, 2010; U.S. patent application Ser. No. 12/805,411, filed Jul. 29, 2010; U.S. Pat. Nos. 6,917,726; 7,170,050; and 7,486,865; and Eid, J., et al., SCIENCE, 323: 133-138 (2009). Two other suitable detection systems are described in U.S. Pat. No. 7,767,441 and U.S. patent application Ser. No. 13/046,457. In some embodiments, the detection system comprises an illumination source, a detector, and a waveguide. In some embodiments, the waveguide comprises a nanowell or other microfluidic structure that can hold a sequencing complex in a volume small enough for selective imaging of the reaction site where polymerization occurs. In other embodiments, the detection system may comprise a movable light coupler, a detector, and a waveguide, wherein the waveguide comprises an adapter site for the movable light coupler. The detection system may perform sequential or simultaneous detection of sequencing sites. In some embodiments, the small size or footprint of an individual nanowell facilitates highly efficient parallelization of sequencing, which can increase throughput and/or sensitivity. For example, a detection system may comprise one or more waveguides that each encompass hundreds to thousands of adapter sites.

The light source embodied in a detection system can be configured to emit light, which may then be at least partially coupled into the waveguide as an excitation light to excite the object. The light source may be, for example, laser such as He—Ne laser and laser diode (LD), light emitting diode (LED), organic light emitting diode (OLED), quantum dot light emitting diode (QLED), fiber light, or arc discharge fluorescent lamp. The detection system may comprise a light source coupler. The light source coupler may couple at least part of the light emitted from the at least one light source into the waveguide. The light source coupler may be, e.g., a prism coupler, a grating coupler, a side-injection coupler, a vertical-injection coupler, or a co-directional coupler. FIG. 1 depicts an example of a detection system suitable for this invention, comprising a controller unit that controls a light source, which produces light that passes through a waveguide to illuminate a sample, and light emitted from said sample is detected by a light detector, which produces a data signal that may optionally be transmitted to an external device, such as a computer server. Optionally, there may be two-way communication between the controller unit and the computer server, such as to allow remote access or control.

2.1 Waveguide

The waveguide may be a channel waveguide or a planar waveguide. The waveguide may comprise a core layer and at least one cladding layer. For example, if the waveguide is a channel waveguide, it may comprise a core layer and a cladding layer surrounding the core layer. As another example, if the waveguide is a planar waveguide, it may comprise a core layer and one cladding layer arranged on the core layer or two cladding layers sandwiching the core layer. The core layer may have a higher refractive index than the at least one cladding layer. The excitation light may propagate in the core layer of the waveguide. Exemplary waveguides and specific features thereof suitable for use in the detection system are described in U.S. patent application Ser. No. 12/720,352, filed Mar. 9, 2010; U.S. patent application Ser. No. 12/801,503, filed Jun. 11, 2010; and U.S. patent application Ser. No. 12/805,411, filed Jul. 29, 2010.

The detection system may comprise a waveguide comprising at least one adapter site for a movable light coupler, described in more detail below. The adapter site may be formed in at least the at least one cladding layer of the waveguide. The adapter site may be a nanowell comprising an upper opening and a bottom surface, wherein the upper opening may be larger than the bottom surface. The nanowell may extend through partial thickness of the at least one cladding layer, full thickness of the at least one cladding layer, full thickness of the at least one cladding layer and partial thickness of the core layer, or the full thickness of the at least one cladding layer and full thickness of the core layer. The lower boundary of the effective excitation zone may be the bottom of the nanowell. The upper boundary of the effective excitation zone may be defined by the distance to which the excitation light can reach in the nanowell adapter site in the direction perpendicular to the longitudinal direction of the core layer (e.g., vertical direction).

The waveguide component of the detection system may comprise a plurality of adapter sites. Therefore, the system may also be used to monitor a large number of objects. In some embodiments, a plurality of adapter sites may be formed in the waveguide. In some embodiments, for each of the plurality of adapter sites, a light detector may be formed to detect the light emitted from an object in the effective excitation zone of the adapter site. In some embodiments, one light detector may be used to detect the light emitted from objects in the effective excitation zones of a plurality of adapter sites.

2.2 Movable Light Coupler

Embodiments of the detection system encompass a movable light coupler which is able to localize a single-molecule object to the at least one adapter site of the waveguide. The movable light coupler may be a nano-scale particle. The movable light coupler may be a nano-scale sphere or a nonspheroidal nano-scale particle. When a movable light coupler docks at an adapter site in the waveguide, a confined excitation space suitable for single-molecule detection (an effective excitation space) may then form, and the object to be detected may be localized within the confined space. When a movable light coupler docks at an adapter site, it may prevent a second movable light coupler from docking at the same adapter site.

The movable light coupler may comprise at least one property by which the light coupler may be attracted to the adapter site, including, for example, a surface property or a magnetic property to facilitate docking. In some embodiments, the light coupler comprises at least one property by which the light coupler may be localized at the at least one adapter site in a specific orientation. Suitable properties by which the light coupler may be localized at the at least one adapter site in a specific orientation may include asymmetric surface properties. In some embodiments, the light coupler can localize a single-molecule object in a confined space near the surface of the core layer of the waveguide within the adapter site, wherein an object is localized in an effective excitation zone formed within the adapter site from a light field induced by a light wave propagating along the core layer of the waveguide.

The movable light coupler may be a homogenous solid, a colloidal or porous solid, or a solid composed of a material with a polymer backbone. In some embodiments, the multifunctional movable light coupler comprises one or more metal materials, including, for example, gold (Au), silver (Ag), cupper (Cu), platinum (Pt), nickel (Ni), chromium (Cr), or a metal alloy. In some embodiments, the light coupler comprises one or more oxide materials, including, for example $TiO_2$, $Ta_2O_5$, $Nb_2O_5$, $SiO_2$, $HfO_2$, $Al_2O_3$, $ZrO_2$, $ZnO$, $V_2O_5$, $CeO_2$, $CdO$, $Fe_2O_3$, $Fe_3O_4$, $Cu_2O$, $CuO$, $In_2O_3$, $La_2O_3$, $MoO_3$, or $WO_3$. In further embodiments, the light coupler comprises one or more sulfide materials, including, for example, CdS, ZnS, PbS, $Au_2S$, or $Ag_2S$. In some embodiments, the light coupler comprises one or more selenide materials, including, for example, CdSe, ZnSe, or PbSe. In some embodiments, the light coupler comprises one or more nitride materials, including, for example, $Si_3N_4$, TiN, BN, and GaN. In further embodiments, the light coupler comprises one or more polymer materials, including, for example, polystyrene, a polyethyleneimine, a polyphosphazene, polylactide, polylactide-co-glycolide, polycaprolactone, a polyanhydride, polymaleic acid and its derivatives, polyalkylcyanoacrylate, polyanhydride oxybutyrate, polycarbonate, polyorthoester, polyethylene glycol, poly-L-lysine, polyglycolide, polymethylmethacrylate, polyvinylpyrrolidone, or copolymers thereof.

In some embodiments, the movable light coupler is made from a material having a refractive index that is closer to the refractive index of the material of the first cladding layer of the waveguide than to the refractive index of the material of the core layer of the waveguide. In some embodiments, the movable light coupler is made from a material having a refractive index that is closer to the refractive index of a surrounding sample solution than to the refractive index of the material of the core layer of the waveguide. In some embodiments, the movable light coupler is made from a material having a refractive index that is intermediate between the refractive index of the first cladding layer of the waveguide and the refractive index of the core layer of the waveguide. In further embodiments, the light coupler is made from a material having a refractive index that is substantially similar to the refractive index of the core layer of the waveguide. In some embodiments, the light coupler is made from a material having a refractive index that is equivalent to the refractive index of the core layer.

In some embodiments, the movable light coupler has an appropriate size and a refractive index sufficiently similar to the refractive index of the material of the core layer of the waveguide such that the light coupler is able to couple light from a waveguide when placed at an adapter site in the waveguide. In such embodiments, an induced light field may form around the surface of the movable light coupler, thereby forming an effective excitation zone around the light coupler, wherein a molecule can be excited to emit fluorescent light within a certain distance of the surface of the light coupler.

In some embodiments, the movable light coupler is opaque and can confine excitation light at its surface, whereby the confined space suitable for single-molecule detection is formed by the movable light coupler blocking the excitation light from the waveguide from spreading to the bulk space. In some embodiments, the movable light coupler is reflective to light. In some embodiments, the movable light coupler is reflective to excitation light. In some embodiments, the movable light coupler is able to absorb excitation light emitted by the waveguide and then itself emit a light which is able to excite molecules to be detected.

In some embodiments, an optical property of the light coupler changes when the light coupler is surrounded by certain molecules within a specific range. In some embodiments, the optical property that changes when the light coupler is surrounded by certain molecules within a specific range is refractive index, light-absorbing capability, the wavelength of light absorbed by the coupler, or the direction of light propagating through the light coupler.

Figure 2:
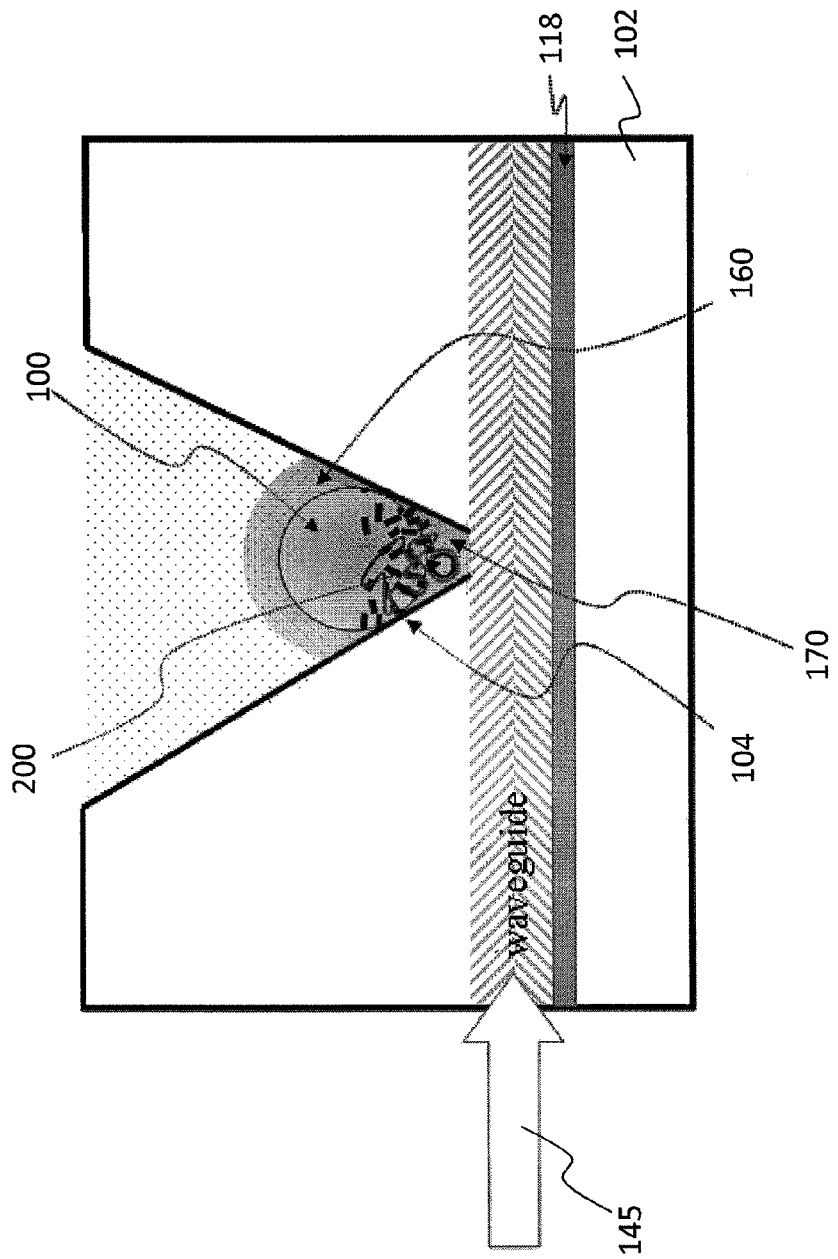
FIG. 2 depicts an exemplary detection system comprising a nano-scale sphere light coupler particle which is modified on one hemisphere with oligonucleotide primers. The nano-scale sphere light coupler 100 is modified on one half of its surface with oligonucleotide primers capable of hybridizing to sequences embedded in a replicating DNA strand of a DNA synthesizing reaction complex 200. Positioning of a light coupler 100 at an adapter site 104 of a waveguide with the oligonucleotide-modified surface of the light coupler facing the core layer of the waveguide localizes the reaction complex 200 in a confined space 170 in the bottom of the nanowell adapter site 104. In such embodiments, the light coupler may couple an evanescent light field induced near the surface of the core layer in the adapter site when an excitation light 145 provides a light wave which propagates along the core layer of the waveguide, thereby forming an effective excitation zone 160 in the confined space between the movable light coupler and the core layer of the waveguide and around the surface of the light coupler. An optical filter is denoted by 118, and a detector is denoted by 102. See U.S. patent application Ser. No. 13/046,457.

In some embodiments, one or more regions of the surface of the movable light coupler are modified. For example, the entire surface of a nano-scale sphere light coupler may be modified. Surface modification is distinct from the shell material of a light coupler with a core-shell structure, i.e., a core-shell light coupler comprising surface modification has modification of the outside surface of the shell material. In a further example, the surface of one hemisphere of a nano-scale sphere light coupler may be modified while the remaining hemisphere is unmodified. The surface of the light coupler may be coated over its entire surface or at least a portion of its surface with one or more heterogeneous materials by chemical modification techniques. A surface modification may serve to localize the movable light coupler at an adapter site. Asymmetric surface modification, e.g., modification on one surface only, or different modification on opposite surfaces, may serve to localize the movable light coupler at an adapter site in a specific orientation. A surface modification may also serve to localize a single-molecule object at a particular region of the surface of the light coupler, whereby such a region may be oriented to face the core layer of the waveguide, thereby localizing the object and any reaction involving the object in a confined space between the movable light coupler and the surface of the adapter site near the core layer of the waveguide. A schematic illustration of an exemplary detection system comprising a nano-scale sphere light coupler particle which is modified on one hemisphere with oligonucleotide primers is shown in FIG. 2. The nano-scale sphere light coupler 100 is modified on one half of its surface with oligonucleotide primers capable of hybridizing to sequences embedded in a replicating DNA strand of a DNA synthesizing reaction complex 200. Positioning of the light coupler 100 at the adapter site 104 with the oligonucleotide-modified surface of the light coupler facing the core layer of the waveguide localizes the reaction complex 200 in the confined space 170 in the bottom of the nanowell adapter site 104.

In some embodiments, only one region of the surface of the movable light coupler is modified, while the remainder of the surface of the light coupler is unmodified. In some embodiments, the modified region of the surface of the movable light coupler is from about 10 to 90% of the surface of the movable light coupler. "About 10 to 90% of the surface of the movable light coupler" as used to describe such embodiments is meant to signify that the modified region of the surface of the movable light coupler may be anywhere from slightly less than 10% to slightly more than 90% of the surface of the light coupler. In further embodiments, the modified region of the surface of the light coupler is less than 10% of the surface of the light coupler. In yet further embodiments, the modified region of the surface of the light coupler is more than 90% of the surface of the light coupler.

In some embodiments, during operation, some of a plurality of detection sites contain one target nucleic acid molecule (optionally attached to a light coupler), and other detection sites do not contain a target nucleic acid molecule. This may prevent the scenario that two or more nucleic acid molecules localize at a detection site before sequencing is completed, so as to prevent the results of one sequencing from comprising information from more than one molecule. For example, in some embodiments, less than or equal to 50%, 40%, 30%, 25%, 20%, 15%, 10%, 9%, 8%, 7%, 6%, 5%, 4%, 3%, 2%, or 1% of the detection sites will generate a signal due to the low concentration of the biological molecules localized at detection sites to be detected or identified. In instances in which a first target nucleic acid dissociates from a detection site, and a second nucleic acid subsequently associates with the same detection site, the results of sequencing the first nucleic acid may be distinguished from the results of sequencing of the second nucleic acid by any gap in the detection of incorporated nucleotides and/or by differences in the determined nucleotide sequences

2.3 Detector

A detector of the subject detection system may be configured to detect light emitted from an object. Such detector may comprise an optical sensor, which is capable of at least partially absorbing light incident thereon and generating output signals in response to the light. The optical sensor can be, e.g., a p-n photodiode, a p-i-n photodiode, a multi-junction photodiode, an avalanche photodiode (APD), a phototransistor, a quantum-well infrared photodetector (QWIP), a photoconductive type optical sensor, a photovoltaic type optical sensor, a thin-film on ASIC (TFA), a metal-semiconductor-metal (MSM) photodetector, a charge coupled device (CCD), a CMOS sensor, or a combination thereof.

In some embodiments, the light detector comprises a control circuit for controlling the operation of the light detector. The control circuit may comprise a circuit of signal amplifier, A/D convertor, integrator, comparator, logic circuit, readout circuit, memory, microprocessor, clock, and/or address.

The light detector may be arranged at a place that the light emitted from the object can reach. For example, the light detector may be arranged at the opposite side of the core layer with respect to the adapter site. That is, if the adapter site is arranged on one side of the core layer in the vertical direction, the light detector may then be arranged on the other side of the core layer in the vertical direction. The detection system may further comprise at least one filter between the core layer and the detector.

In some embodiments, the detector may be a nanopore sensor. Nanopore sensors are created by making small holes about 1 nm in diameter, called nanopores. Nanopores used for detection purposes can be natural (such as transmembrane proteins) or man-made (such as by etching a hole in a silicon sheet and using ion-beam sculpting methods to fill it to create nanopores). Nanopore sensors typically work by immersing a nanopore in a conducting fluid and applying a voltage across it. Any slight electric current due to conduction of ions through the nanopore can be observed, as the amount of current that passes through the nanopore is very sensitive to the size and shape of the nanopore. A molecule, including but not limited to a label moiety cleaved from the nucleotide analog as described in this invention, passing through the nanopore can create a characteristic change in the magnitude of the current through the nanopore.

Passing molecules through the nanopore can be controlled by electrophoresis, wherein a molecule is drawn toward the nanopore. Multiple molecules pass through the nanopore one molecule at a time. As each molecule passes through, it obstructs the nanopore in a manner characteristic of the identity of the molecule; that is, the amount of current passing through the nanopore in a given moment depends on the molecule blocking the nanopore at that moment. Different labels on the nucleotide analogs of this invention would allow different currents to pass through the nanopore when the excised labels pass through the nanopore, allowing identification of the order of labels passing through the nanopore, and thus allows identification of the target sequence. Nanopore sensors are further disclosed by the publications Howorka, et al., Nature Biotechnology, 19: 636-639 (2001); Clarke, et al., Nature Nanotechnology, 4: 265-270 (2009); and U.S. Pat. Nos. 5,795,782; 6,362,002; 6,123,819; and 6,413,792.

2.4 Other Optional Components of the System

In some embodiments, the detector system may further comprise an optical filter between the core layer of the waveguide and the light detector. In some embodiments, an optical filter may be arranged between a lower cladding layer of the waveguide and the light detector. In some embodiments, an optical filter may be arranged between a lower protection layer of the waveguide and the light detector. In some embodiments, the lower protection layer itself may serve as an optical filter. An optical filter may allow a light with a wavelength within a certain range to pass through but at least partially block a light with a wavelength outside the certain range. Therefore, an optical filter may be selected to allow the light emitted from the sequencing complex to pass through but the noise caused by the excitation light is reduced, so as to improve the S/N ratio.

In some embodiments, a microfluidic channel may be used to conduct the sample solution into the adapter site. The microfluidic channel may be designed in a way that the target objects pass through the adapter site one at a time, so as to realize a flow-cytometry-like detection. In some embodiments, a cover may be formed over the detection system to contain the sample solution and/or to block the ambient light. In some embodiments, the detector system may comprise a controller that operates at least a portion of the detection system, including but not limited to a light source, a detector, and any flow or other components of the detection system. The controller may comprise a computer-readable medium that contains instructions regarding the control of various components of the detection system, and may also contain instructions on data processing and analysis. It is to be understood that other components known in the art may be included in the detection system as would be useful for the practice of the invention.

In some embodiments, information concerning signal pulses may be stored in the detection system and optionally retrieved, transmitted, or analyzed concurrent with the sequencing reaction or at a later time. In some embodiments, this information may be transmitted to one or more external devices, including but not limited to computer systems, servers, cell phones, tablet computing systems, distributed computing networks, and other electronic devices capable of storing or processing information. Information may be transmitted concurrently with detection, or may be transmitted subsequent to detection. In some embodiments, the external device comprises a database of sequences, which may be public or private. In some embodiments, the external device analyzes the signal pulse information to produce the sequence of a target nucleic acid. In some embodiments, the external device may perform additional functions, including but not limited to proof reading of base calls, alignment with other sequences, such as a reference sequence, error analysis, report generation, or further transmitting the information to other devices, including transmitting information back to the detection system. In some embodiments, the information and optionally the resulting sequences and analyses may be encrypted. In some embodiments, the information may be encrypted prior to its being transmitted to an external device.

A communication assembly may be housed within the detection system and is capable of transmitting and receiving information from an external device. Such communication may be through a wired network or wirelessly. Various communication methods can be utilized, such as through an Ethernet or other local area network, a USB connection, a FireWire connection, dial-up wired connection with a modem, a direct link such as a T1, ISDN, or cable line. Wireless communication may be Bluetooth or RTM technology. In preferred embodiments a wireless connection is established using exemplary wireless networks such as cellular, satellite, or pager networks, GPRS, or a local data transport system such as Ethernet or token ring over a local area network. In some embodiments, the information may be sent to a personal address, including but not limited to a phone number, a text messaging address, an email address, or an online account. In some embodiments the communication assembly may contain a wireless infrared communication component for sending and receiving information.

3.1 Example 1

In this and the following examples, exemplary nucleotide analogs may comprise bases $B_1$, $B_2$, and/or groups $L_1$, $L_2$, Q, F, $X_1$, and $X_2$, each having an identity as described herein for nucleotide analogs having a structure of Formula I, supra.

An exemplary binucleotide triphosphate analog has a structure as shown in Formula II:

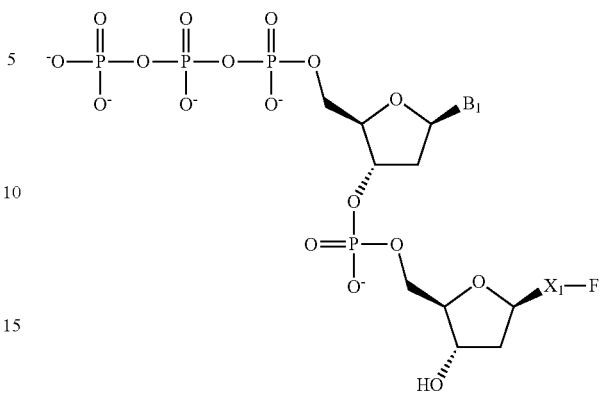

Figure 3:
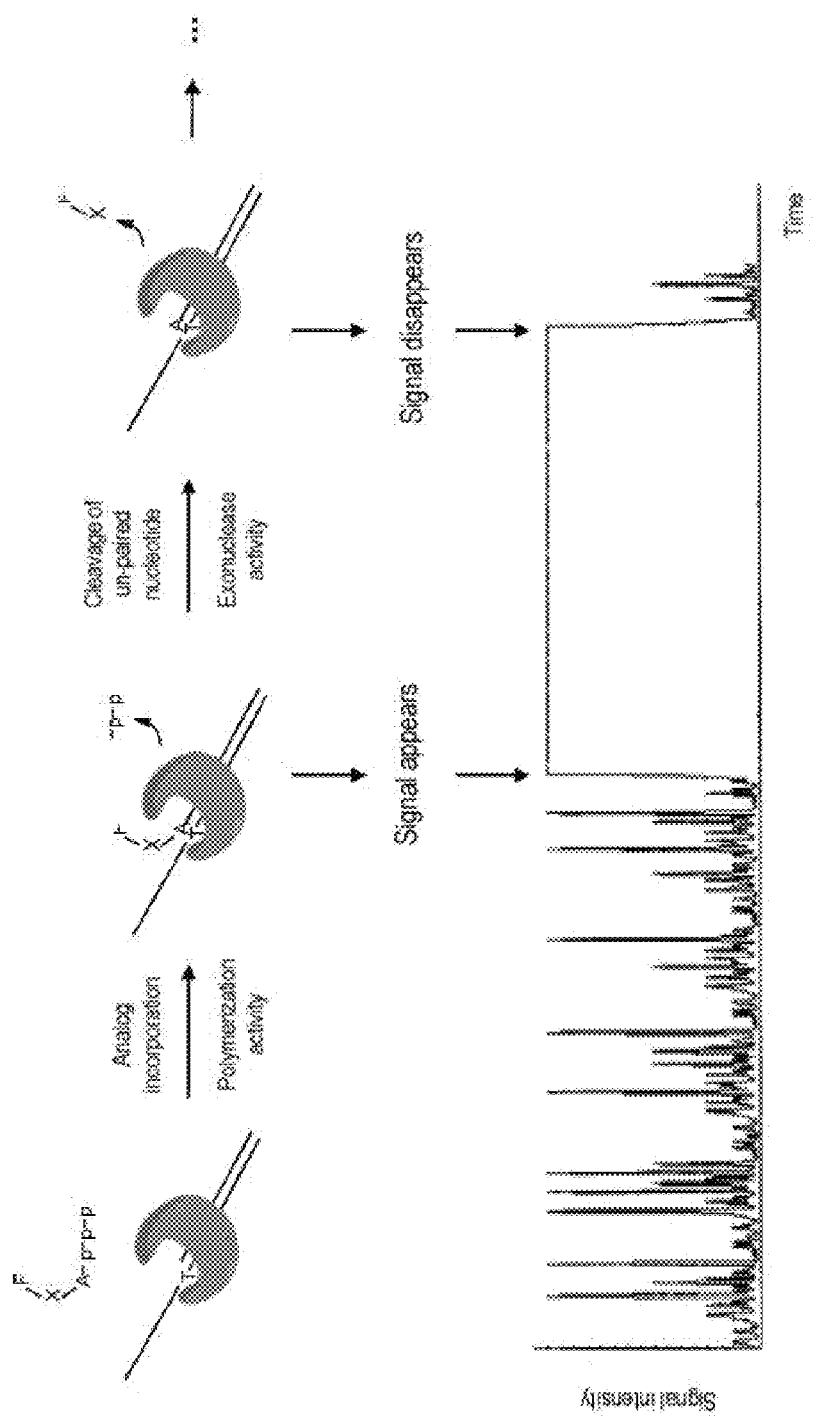
FIG. 3 depicts the lengthening of fluorescent signal pulse width in a step of sequencing by synthesis using a binucleotide analog.

A schematic illustration of a single cycle of proofreading-dependent sequencing by synthesis using an analog having the structure of Formula II is provided in FIG. 3. A reaction complex comprising a proofreading polymerase, a target (template) strand, and a replicating strand are exposed to excitation light. An incoming binucleotide analog having adenine as base $B_1$ associates with the reaction site of the polymerase and base pairs with a thymine base in the target strand. The binucleotide analog is incorporated into the growing strand by the polymerase, whereupon the fluorescent label F is excited by the excitation light and emits a signal captured by a detector. As shown in the spectrogram, this signal remains detectable until the unpaired moiety of the analog (comprising group X which is not able to base pair with the subsequent base in the target strand and the fluorescent label F) is cleaved from the growing strand by the exonuclease activity of the polymerase. The signal disappears as the labeled, unpaired moiety of the analog dissociates from the reaction complex.

3.2 Example 2

An exemplary binucleotide triphosphate analog comprising a fluorescence quenching moiety Q has a structure of Formula III:

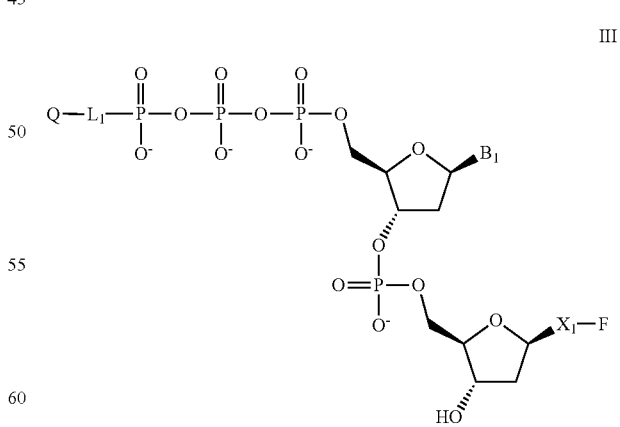

3.3 Example 3

An exemplary binucleotide triphosphate analog with a phosphorothioate in place of the alpha-phosphate of the triphosphate chain, thereby preventing processive 3' to 5' exonuclease activity of polymerase, has a structure as shown in Formula IV:

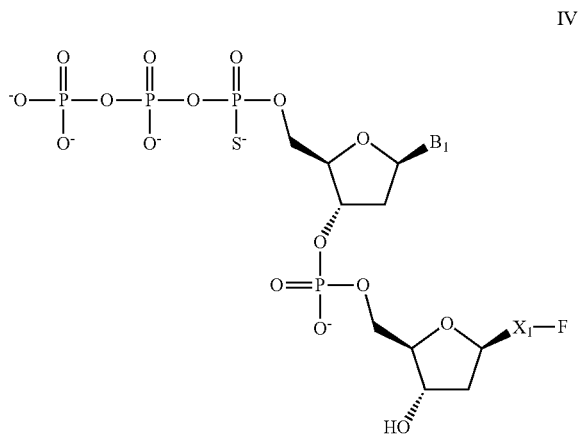

IV

Figure 4:
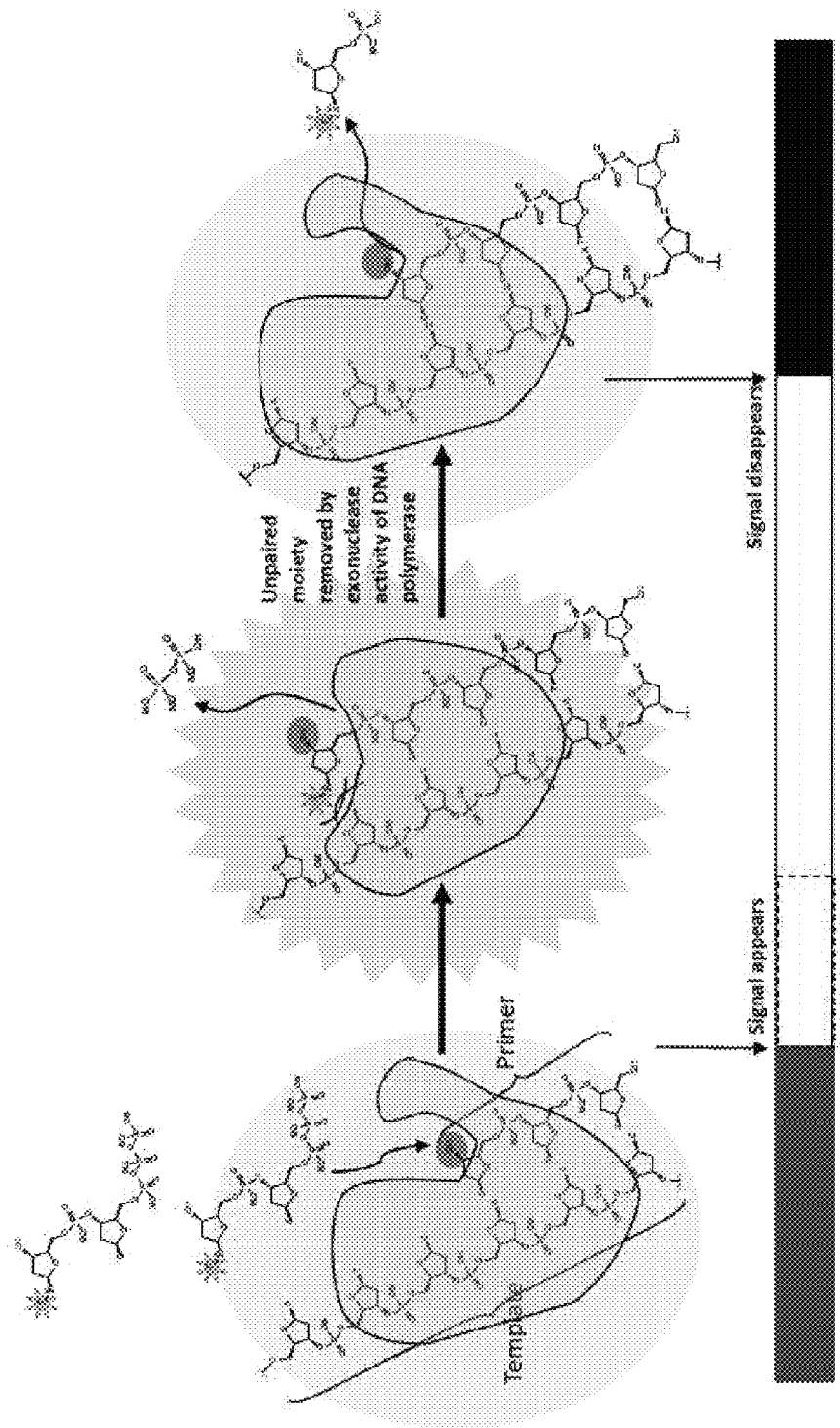
FIG. 4 depicts the pulse duration in a step of sequencing by synthesis using a binucleotide analog.

A schematic illustration of a single cycle of proofreading-dependent sequencing by synthesis using an analog having the structure of Formula IV is shown in FIG. 4. A reaction complex comprising a proofreading polymerase, a target ("Template") strand, and a replicating strand ("Primer") are exposed to excitation light. An incoming binucleotide analog having guanine as base $B_1$ associates with the reaction site of the polymerase and base pairs with a cytosine base in the template strand, whereupon the fluorescent label F is excited by the excitation light and emits a signal captured by a detector. As shown in the bar at the bottom of FIG. 4, depicting signal appearance, this signal remains detectable as the binucleotide analog is incorporated into the growing strand by the polymerase, and continues until the unpaired moiety of the analog (comprising group X which is not able to base pair with the subsequent base in the target strand and the fluorescent label F) is cleaved from the growing strand by the exonuclease activity of the polymerase. The signal disappears as the labeled, unpaired moiety of the analog dissociates from the reaction complex.

3.4 Example 4

An exemplary binucleotide triphosphate analog with a fluorescence quenching moiety Q and a phosphorothioate in place of the alpha-phosphate of the triphosphate chain, thereby preventing processive 3' to 5' exonuclease activity of polymerase, has a structure as shown in Formula V:

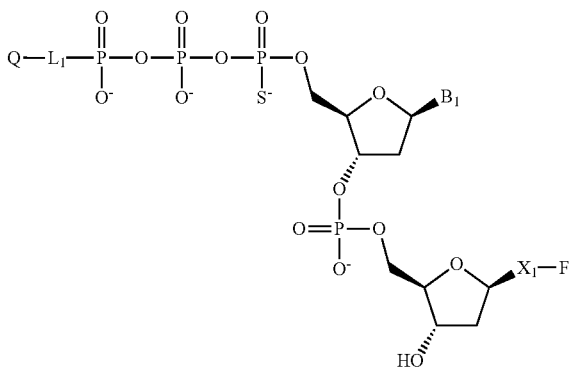

V

Figure 5:
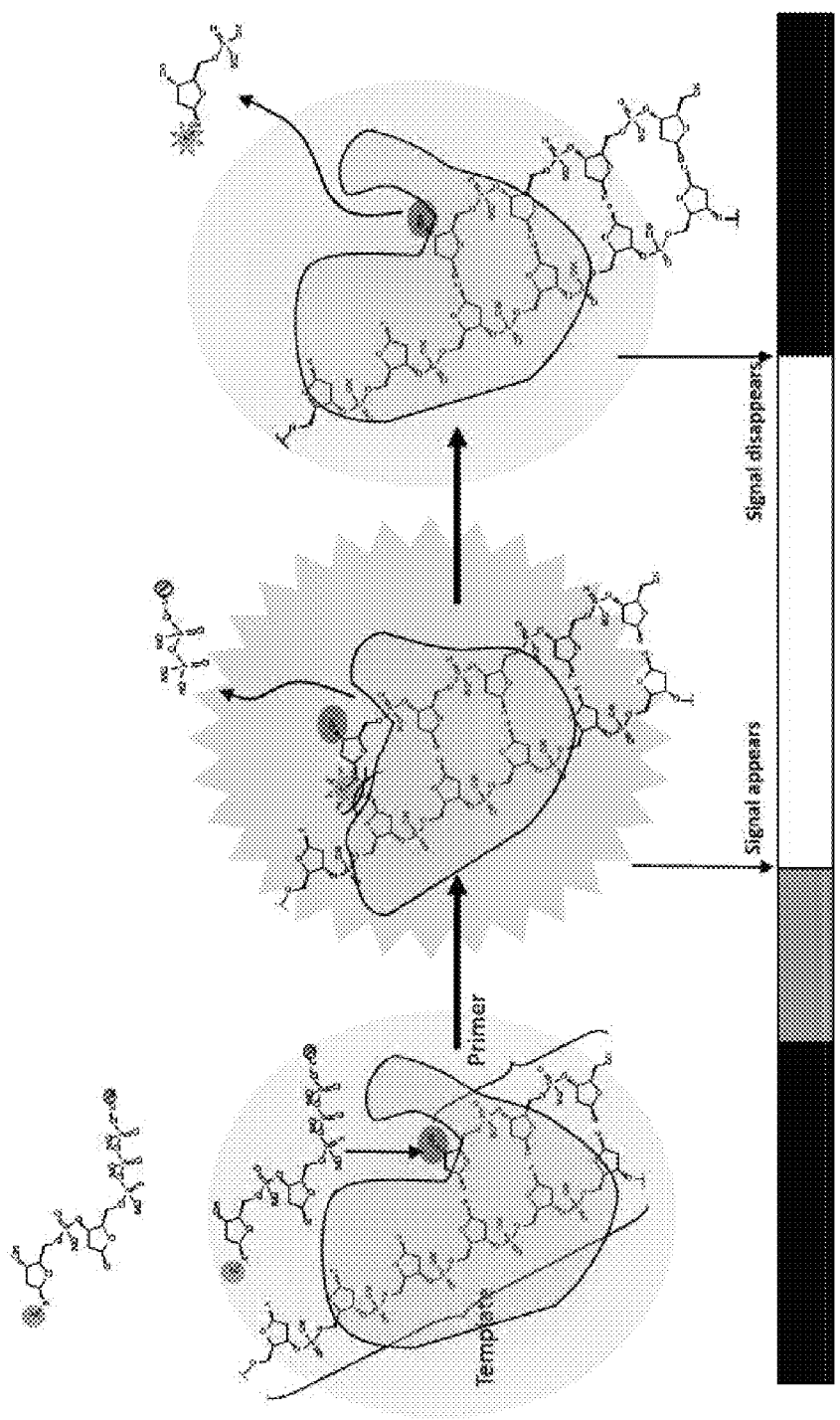
FIG. 5 depicts the pulse duration in a step of sequencing by synthesis using a binucleotide analog comprising a fluorescence quenching moiety. As compared to FIG. 4, the use of the quencher reduces background signal from unincorporated nucleotide analogs and delays the start of the signal until an analog in the reaction site of the polymerase becomes incorporated into the growing nucleotide strand, when the pyrophosphate group comprising the quenching moiety is released.

A schematic illustration of a single cycle of proofreading-dependent sequencing by synthesis using an analog having the structure of Formula V is shown in FIG. 5. A reaction complex comprising a proofreading polymerase, a target ("Template") strand, and a replicating strand ("Primer") are exposed to excitation light. An incoming binucleotide analog having guanine as base $B_1$ associates with the reaction site of the polymerase and base pairs with a cytosine base in the template strand. Fluorescence quenching moiety Q quenches light emitted from excited fluorescent group F until the binucleotide analog is incorporated into the growing strand by the polymerase, whereupon the fluorescent quencher Q attached to pyrophosphate is released from the reaction complex. As shown in the bar at the bottom of FIG. 5, depicting signal appearance, the signal from incorporated fluorescent group F remains detectable until the unpaired moiety of the analog (comprising group X which is not able to base pair with the subsequent base in the target strand and the fluorescent label F) is cleaved from the growing strand by the exonuclease activity of the polymerase. The signal disappears as the labeled, unpaired moiety of the analog dissociates from the reaction complex.

3.5 Example 5

An exemplary mononucleotide triphosphate analog has a structure as shown in Formula VI:

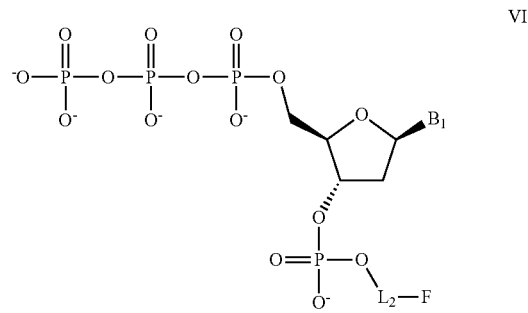

VI

Following incorporation of a mononucleotide triphosphate analog having a structure as shown in Formula VI into a growing nucleic acid strand, the phosphate-$L_2$-F group is removed by the 3' to 5' exonuclease activity of a proofreading polymerase to free the 3'-OH of the incorporated mononucleotide analog for the next step of synthesis.

3.6 Example 6

An exemplary mononucleotide triphosphate analog comprising a fluorescence quenching moiety Q has a structure as shown in Formula VII:

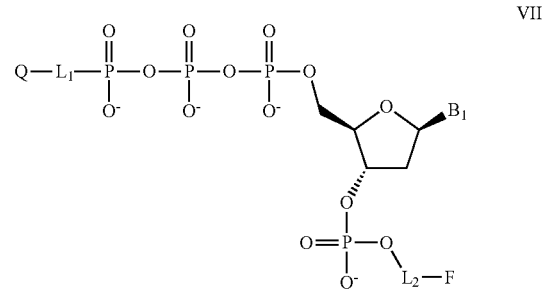

VII

3.7 Example 7

An exemplary mononucleotide triphosphate analog comprising an alpha-phosphorothioate to prevent processive 3' to 5' exonuclease activity of a proofreading polymerase has a structure as shown in Formula VIII:

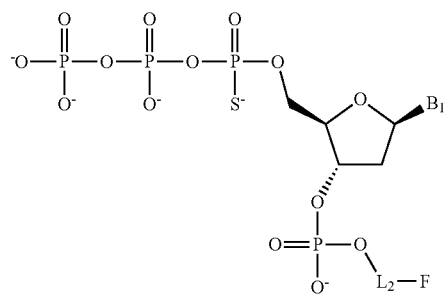

VIII

3.8 Example 8

An exemplary mononucleotide triphosphate analog comprising an alpha-phosphorothioate to prevent processive 3' to 5' exonuclease activity of a proofreading polymerase and comprising a fluorescence quenching moiety Q has a structure as shown in Formula IX:

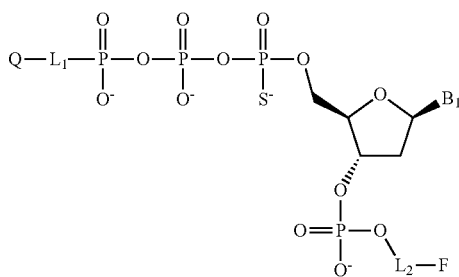

IX

3.9 Example 9

An exemplary trinucleotide triphosphate comprising bases $B_1$ and $B_2$ at its 5' end which are able to base pair with complementary bases in a target nucleic acid and comprising a nucleotide residue at its 3' end which comprises group $X_1$ which is unable to base pair with a complementary base in a target nucleic acid has a structure as shown in Formula X:

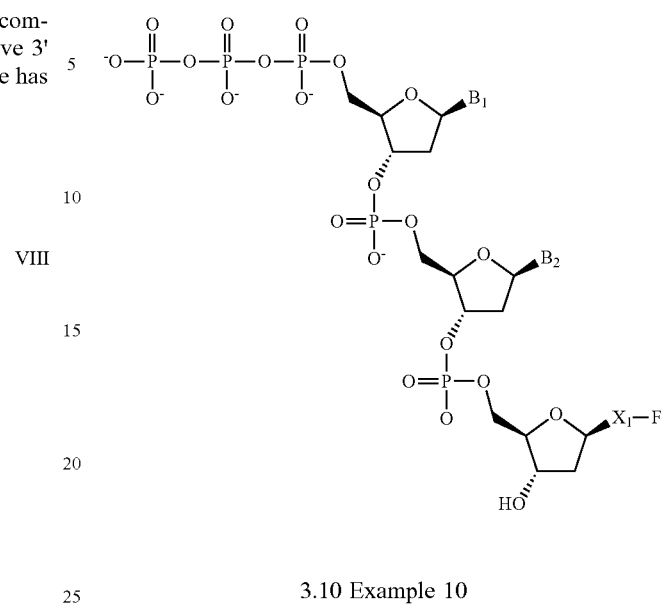

X

3.10 Example 10

An exemplary trinucleotide triphosphate analog comprising (1) bases $B_1$ and $B_2$ at its 5' end which are able to base pair with complementary bases in a target nucleic acid, (2) a nucleotide residue at its 3' end which comprises group $X_1$ which is unable to base pair with a complementary base in a target nucleic acid, and (3) a fluorescence quenching moiety Q, has a structure as shown in Formula XI:

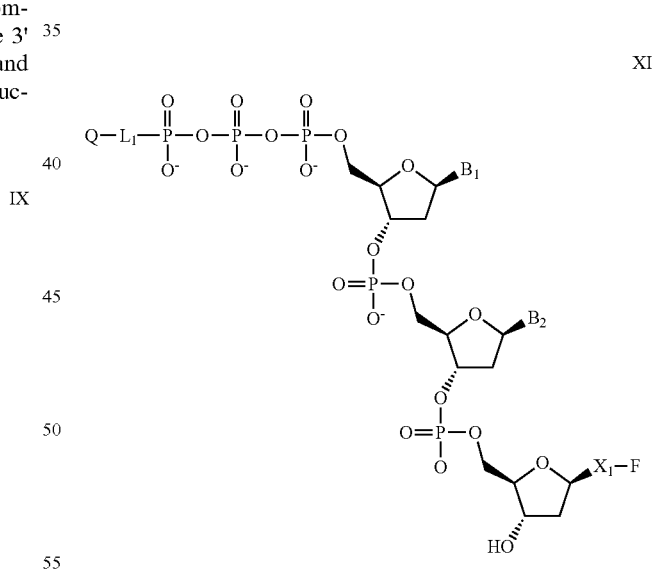

XI

3.10 Example 11

An exemplary trinucleotide triphosphate analog comprising (1) bases $B_1$ and $B_2$ at its 5' end which are able to base pair with complementary bases in a target nucleic acid, (2) a nucleotide residue at its 3' end which comprises group $X_1$ which is unable to base pair with a complementary base in a target nucleic acid, and (3) an alpha-phosphorothioate which prevents processive 3' to 5' exonuclease activity of the polymerase, has a structure as shown in Formula XII:

XII

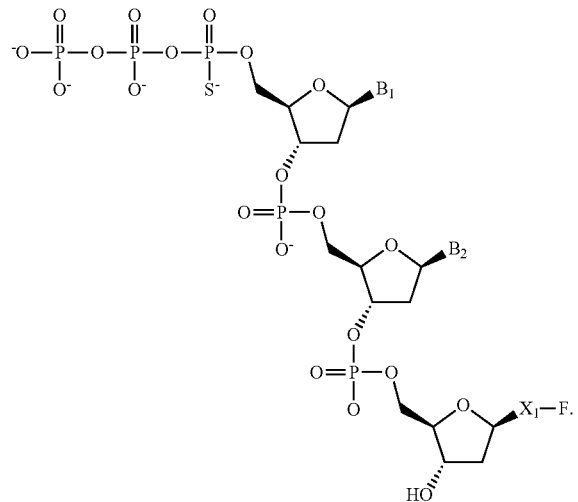

3.12 Example 12

An exemplary trinucleotide triphosphate analog comprising (1) bases $B_1$ and $B_2$ at its 5' end which are able to base pair with complementary bases in a target nucleic acid, (2) a nucleotide residue at its 3' end which comprises group $X_1$ which is unable to base pair with a complementary base in a target nucleic acid, (3) a fluorescence quenching moiety Q, and (4) an alpha-phosphorothioate which prevents processive 3' to 5' exonuclease activity of the polymerase, has a structure as shown in Formula XIII:

XIII

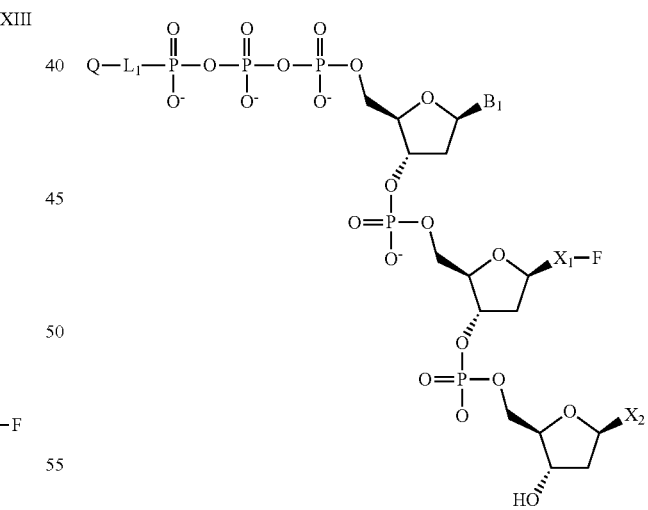

3.13 Example 13

An exemplary trinucleotide triphosphate analog comprising (1) base $B_1$ at its 5' end which is able to base pair with a complementary base in a target nucleic acid, and (2) nucleotide residues at its 3' end which comprise groups $X_1$—F and $X_2$ which are unable to base pair with bases in a target nucleic acid, has a structure as shown in Formula XIV:

XIV

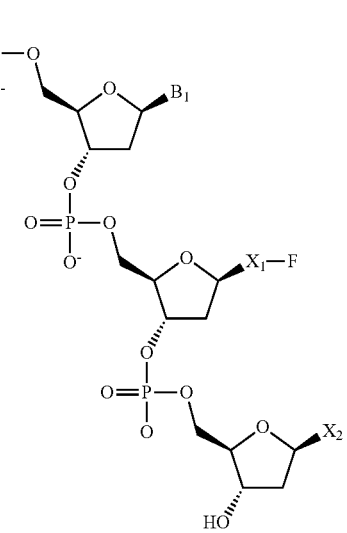

3.14 Example 14

An exemplary trinucleotide triphosphate analog comprising (1) base $B_1$ at its 5' end which is able to base pair with a complementary base in a target nucleic acid, (2) nucleotide residues at its 3' end which comprise groups $X_1$—F and $X_2$ which are unable to base pair with bases in a target nucleic acid, and (3) a fluorescence quenching moiety Q, has a structure as shown in Formula XV:

XV

3.15 Example 15

An exemplary trinucleotide triphosphate analog comprising (1) base $B_1$ at its 5' end which is able to base pair with a complementary base in a target nucleic acid, (2) nucleotide residues at its 3' end which comprise groups $X_1$—F and $X_2$ which are unable to base pair with bases in a target nucleic acid, and (3) an alpha-phosphorothioate which prevents processive 3' to 5' exonuclease activity of the polymerase, has a structure as shown in Formula XVI:

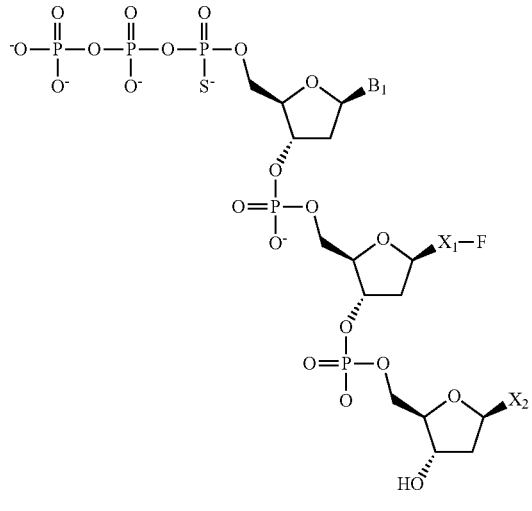

3.16 Example 16

An exemplary trinucleotide triphosphate analog comprising (1) base $B_1$ at its 5' end which is able to base pair with a complementary base in a target nucleic acid, (2) nucleotide residues at its 3' end which comprise groups $X_1$—F and $X_2$ which are unable to base pair with bases in a target nucleic acid, (3) a fluorescence quenching moiety Q, and (4) an alpha-phosphorothioate which prevents processive 3' to 5' exonuclease activity of the polymerase, has a structure as shown in Formula XVII:

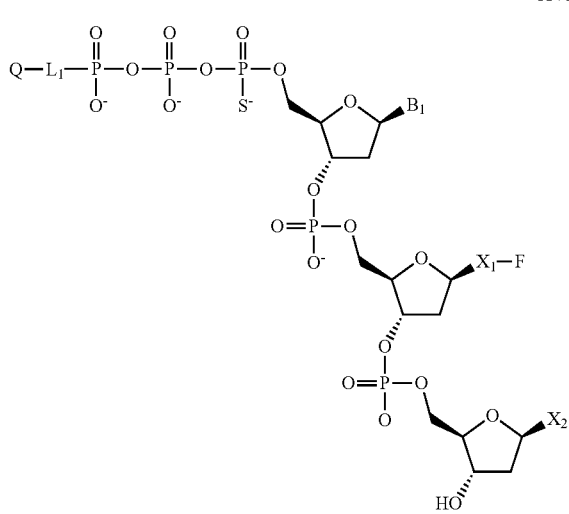

3.17 Example 17

An exemplary trinucleotide triphosphate analog comprising (1) base $B_1$ at its 5' end which is able to base pair with a complementary base in a target nucleic acid, and (2) nucleotide residues at its 3' end which comprise groups $X_1$—F and $X_2$ which are unable to base pair with bases in a target nucleic acid, has a structure as shown in Formula XVIII:

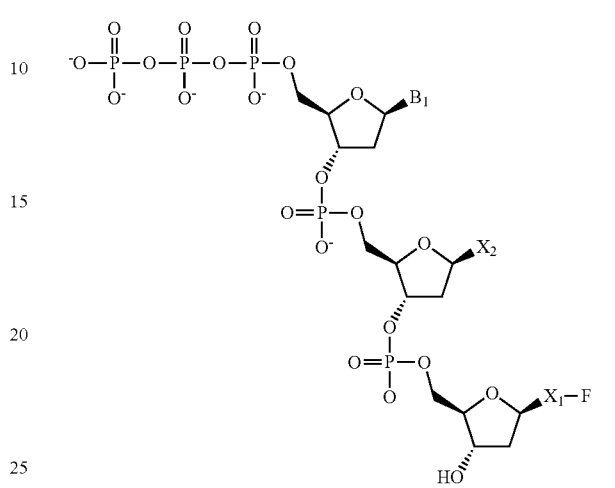

In some embodiments, the trinucleotide triphosphate analog of Formula XVIII has, instead of an alpha-phosphate group, an alpha-phosphorothioate group which prevents processive 3' to 5' exonuclease activity of a proofreading polymerase, in the same manner as the analogs described in Examples 3, 4, 7, 8, 11, 12, 15, and 16. In some embodiments, the trinucleotide triphosphate analog of Formula XVIII comprises a fluorescence quenching moiety Q at the gamma phosphate, in the same manner as the analogs described in Examples 2, 4, 6, 8, 10, 12, 14, and 16.

3.18 Example 18

A DNA molecule is sequenced according to the methods described herein. A solution of circular, single-stranded DNA molecules with an average length of 200 nt at a concentration of 0.1 molecules per attoliter in a suitable sequencing reaction buffer is applied to a detection apparatus as described in U.S. patent application Ser. No. 13/046,457, filed Mar. 11, 2011, entitled "Single-Molecule Detection System and Methods." Alternatively, the solution of circular, single-stranded DNA molecules is applied to a detection apparatus as described in U.S. application Ser. No. 12/801,503, filed Jun. 11, 2010; U.S. patent application Ser. No. 12/805,411, filed Jul. 29, 2010; U.S. Pat. Nos. 6,917,726; 7,170,050; and 7,486,865; and Eid, J., et al., SCIENCE, 323: 133-138 (2009).

The circular DNA molecules contain a known insert sequence of approximately 20 nucleotides 3' to an unknown sample sequence. A sequencing primer complementary to the known insert sequence and four types of fluorescently labeled binucleotide analogs are provided, wherein each of the four binucleotide analogs comprises a complementary base $B_1$ which is adenine, cytosine, guanine, or thymine, respectively. In a plurality of detection sites in the detection apparatus, a ternary complex of a proofreading polymerase, DNA molecule, and sequencing primer is formed and the polymerase adds one fluorescently labeled nucleotide analog to the 3' end of the sequencing primer.

In the plurality of detection sites, a fluorescently labeled binucleotide analog which associates with the reaction site of the polymerase and is incorporated into the growing (primer) strand is excited by excitation light from a light source coupled to the detection apparatus and emits fluorescent light. This fluorescent light is detected by the detection apparatus, which generates output signals to be processed to identify the base comprised by the binucleotide analog added to the sequencing primer. The fluorescent signal disappears when the polymerase cleaves the non-complementary nucleotide group which comprises the fluorescent label from the growing strand, leaving the 3'-OH of the complementary group comprising base $B_1$ free for the next nucleotide analog incorporation.

The polymerase then adds another binucleotide analog, which is detected as above. This cycle is repeated a sufficient number of times to acquire a sequencing read at least twice the length of the DNA molecule (i.e., the DNA molecule is sequenced and resequenced). The sequence of the DNA molecule is then obtained computationally by accepting or rejecting sequencing repeats and determining a consensus sequence from an alignment of the accepted repeats, as described in U.S. Pat. Pub. No. 2010/0121582, published May 13, 2010.

3.19 Example 19

The genome of lambda phage is sequenced herein. The purified, linear genome is suspended at 0.1 molecules per attoliter in a suitable reaction buffer and applied to a detection system as described in U.S. patent application Ser. No. 13/046,457. Alternatively, the genome may be purified in circular form or ligated to form a circular structure. In either case, heat is used to denature the double-stranded lambda genome to form a single template strand ready for sequencing.

A sequencing primer is designed to complement one end of the linearized template strand, or in the case of the circularized genome, the primer complements any known sequence on the template strand. The primer is suspended at a concentration of approximately 1 molecule per attoliter and applied to the detection system, along with a proofreading processive polymerase and four types of fluorescently labeled binucleotide analogs, wherein each of the four binucleotide analogs comprises a complementary base $B_1$ which is adenine, cytosine, guanine, or thymine, respectively. The binucleotide analogs further comprise a fluorescence quencher linked to the gamma phosphate group. In a plurality of detection sites in the detection apparatus, a ternary complex of a proofreading polymerase, DNA molecule, and sequencing primer is formed and the polymerase adds one fluorescently labeled nucleotide analog to the 3' end of the sequencing primer.

In each of the plurality of detection sites, incorporation of a fluorescently labeled binucleotide analog at the reaction site of the polymerase into the growing (primer) strand includes cleavage of the fluorescent quencher from the binucleotide analog. The fluorescent label on the binucleotide analog is excited by excitation light from a light source coupled to the detection apparatus and emits fluorescent light. This fluorescent light is detected by the detection apparatus, which generates output signals to be processed to identify the base comprised by the binucleotide analog added to the sequencing primer. The fluorescent signal disappears when the 3' to 5' exonuclease activity of the polymerase cleaves the non-complementary nucleotide group which comprises the fluorescent label from the growing strand, leaving the 3'-OH of the complementary group comprising base $B_1$ free for the next nucleotide analog incorporation.

The polymerase then adds another binucleotide analog, which is detected as above. This cycle is repeated a sufficient number of times to acquire a sequencing read up to the length of the genome (about 48 kb). The sequencing reaction is then heated or treated with high salt to remove the newly synthesized strand, washed, and the sequencing mix is re-added for a second sequencing read. Alternatively, instead of obtaining a full sequence during each read, the initial read may cover only a subset of the lambda genome. Following the wash step, a different sequencing primer is included in the sequencing reaction to sequence a second, overlapping section of the lambda genome. These steps are repeated until 2× coverage of the entire genome is achieved. The sequence of the DNA molecule is then obtained computationally by accepting or rejecting sequencing repeats and determining a consensus sequence from an alignment of the accepted repeats, as described in U.S. Pat. Pub. No. 2010/0121582, published May 13, 2010.

3.20 Example 20

One example of a detection system utilizes a nano-sphere movable light coupler modified with magnetic functional groups on a portion of its surface for attaching the target sequence. The nano-sphere particle is chemically modified with streptavidin on the magnetically modified surface. Biotinylated oligonucleotide primers comprising a sequence complementary to the sequence of the sequencing primer (the linking nucleic acid molecule) are combined with the streptavidin-modified nano-sphere, thereby linking the biotinylated primers to the nano-sphere. The target sequence is then hybridized to the biotinylated primer and the DNA polymerase is added to form a reaction complex. The movable light coupler is deposited in a nanowell such that the bottom of the nano-sphere confines the target sequence and primer within an attoliter volume at the base of the nanowell in a waveguide (the adapter site) by use of micro-fabricated coils located underneath the adapter site. Passing an electric current through the micro-fabricated coils generates a magnetic field which traps the nano-sphere with adsorbed reaction complex at the adapter site, with the magnetically-modified surface with adsorbed reaction complex facing the core layer of the waveguide. Thus, the reaction complex is localized at the adapter site in the confined space near the surface of the core layer of the waveguide.

DNA synthesis with the binucleotide or trinucleotide analogs described in the examples above is performed in the adapter site. At each step of the synthesis reaction, one of the four types of labeled dNTPs associates with the reaction site of the reaction complex, where it base pairs with the corresponding base of the target nucleic acid. The fluorescent label is excited by the evanescent light field formed at the bottom of adapter site and/or by the evanescent light field radiating from the surface of the nano-sphere. Incorporation of a fluorophore-labeled nucleotide polyphosphate into the growing nucleotide strand at the reaction site is detected in real-time by detecting emission of the dNTP-linked fluorophore. The identity of each incorporated nucleotide is determined by its fluorescent label, wherein the fluorescence label is then cleaved from the nucleotide upon incorporation into the growing strand. The sequence of the target nucleic acid is derived by converting the sequence of the fluorescence emission signals detected during the polymerization reaction into a nucleic acid sequence.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications, patent applications, and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. The recitation of series of numbers with differing amounts of significant digits in the specification is not to be construed as implying that numbers with fewer significant digits given have the same precision as numbers with more significant digits given.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize, or be able to ascertain using no more than routine experimentation, many equivalents to the specific embodiments described herein. Such equivalents are intended to be encompassed by the following claims.

Unless defined otherwise, all technical and scientific terms used herein have the same meaning as commonly understood by one of ordinary skill in the art to which the invention belongs. Any methods and materials similar or equivalent to those described herein can be used in the practice or testing of the invention.

The publications discussed herein are provided solely for their disclosure prior to the filing date of the present application. Nothing herein is to be construed as an admission that the invention is not entitled to antedate such publication by virtue of prior invention. Further, the dates of publication provided may be different from the actual publication dates which may need to be independently confirmed.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A method of determining the nucleotide sequence of a target nucleic acid sequence, comprising the steps of
   (a) providing a reaction complex comprising a template nucleic acid comprising a target nucleic acid sequence, a primer nucleic acid comprising a. sequence which is complementary to a region of the template nucleic acid, and a polymerase enzyme or an enzyme complex, which comprises 5' to 3' polymerization activity and 3' to 5' exonuclease activity;
   (b) contacting the reaction complex with a plurality of nucleotide analogs, Wherein at least one nucleotide analog of said plurality comprises at least one base-pairing moiety, at least one non-complementary nucleotide residue and at least one label moiety comprising a photo-detectable label that is indicative of the identity of the base-pairing moiety, further wherein the at least one nucleotide analog of said plurality is chosen from compounds having formula I:

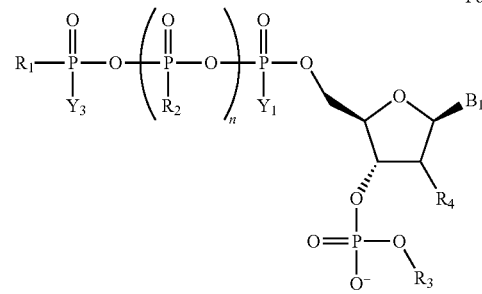

Formula I or a pharmaceutically acceptable salt or hydrate thereof, wherein n is 1, 2, 3, 4, 5, 6, 7, 8, or 9;

$R_1$ and each $R_2$ are $O^-$; or $R_1$ is

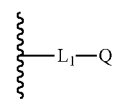

and each $R_2$ is $O^-$; or $R_1$ is $O^-$, one $R_2$, is

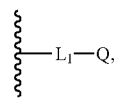

and any remaining $R_2$ is independently $O^-$, $S^-$, $BH_3^-$, or $CH_3$;

$R_3$ is chosen from:

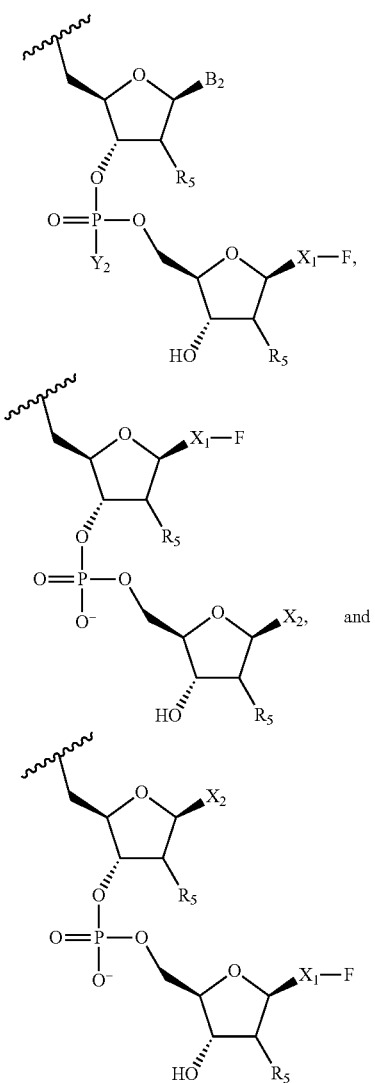

wherein:
- $B_2$ is chosen from adenine, cytosine, guanine, thymine, uracil, hypoxanthine, and 5-methylcytosine;
- $X_1$ is chosen from methylene; $L_2$; a base which does not base pair with any of adenine, cytosine, guanine, thymine, and uracil; and groups comprising $L_2$ and a base which does not base pair with any of adenine, cytosine, guanine, thymine, and uracil; wherein $L_2$ is chosen from alkyl, alkenyl, alkynyl, aryl, heteroaryl, heterocyclyl, ester, amino, and sulfonyl;
- $X_2$ is chosen from H, $CH_3$, and a base which does not base pair with any of adenine, cytosine, guanine, thymine, and uracil;
- each $R_5$ is independently H, OH, fluorine, or $OCH_3$;
- $Y_2$ is chosen from $O^-$, $S^-$, $BH_3^-$, and $CH_3$
- F is a fluorescent dye;
- $R_4$ is H, OH, halogen, alkyl (both substituted and unsubstituted), or alkoxy (both substituted and unsubstituted);
- $Y_1$ and $Y_3$ are each independently chosen from $O^-$, $S^-$, $BH_3^-$, and $CH_3$;
- $L_1$ is chosen from alkyl, alkenyl, alkynyl, aryl, heteroaryl, heterocyclyl, ester, amino, and sulfonyl;
- Q is a fluorescence quenching moiety; and
- $B_1$ is chosen from adenine, cytosine, guanine, thymine, uracil, hypoxanthine, and 5-methylcytosine;

(c) allowing the enzyme or enzyme complex to incorporate a nucleotide analog in a template-dependent manner into a nascent strand via the enzyme's or enzyme complex's 5' to 3' polymerization activity, whereby the label moiety of the nucleotide analog is coupled to the nascent strand;

(d) detecting the photo-detectable label of the incorporated nucleotide analog;

(e) allowing the enzyme or enzyme complex to remove the label. moiety of the incorporated nucleotide analog from the nascent strand via the enzyme's or enzyme complex's 3' to 5' exonuclease activity; and (f) repeating steps (c)-(e) to determine the sequence of the target nucleic acid sequence.

2. The method of claim 1, wherein the photo-detectable label is a fluorophore.

3. The method of claim 2, wherein at least one of said plurality of nucleotide analogs comprises at least one fluorescence quenching moiety, and wherein the fluorescence quenching moiety is removed from the nucleotide analog upon incorporation of the nucleotide analog via the enzyme's or enzyme complex's 5' to 3' polymerization activity into the nascent strand.

4. The method of claim 1, wherein the at least one base-pairing moiety, having a 5' end and a 3' end, comprises one or more nucleotide residues that each comprises a base that is able to base pair with a corresponding base of the target nucleic acid sequence in an active site of the reaction complex.

5. The method of claim 4, wherein the 3' end of the base-pairing moiety is connected to the label moiety via a phosphate linkage.

6. The method of claim 3, wherein the fluorescence quenching moiety is attached to the 5' end of a nucleotide analog.

7. The method of claim 6, wherein the fluorescence quenching moiety is attached to the 5' end of the nucleotide analog via a linker.

8. The method of claim 6, wherein the nucleotide analog is a nucleotide triphosphate analog having an alpha phosphate, a beta phosphate and a gamma phosphate, and wherein the fluorescence quenching moiety is attached to the beta or gamma phosphate of the triphosphate group at the 5' end of the nucleotide analog.

9. The method of claim 4, wherein the at least one base-pairing moiety comprises at least three phosphate groups at its 5' end, wherein the phosphate group most proximal to the base-pairing moiety (the alpha phosphate) is a phosphorothioate.

10. The method of claim 4, wherein the at least one base-pairing moiety comprises at least three phosphate groups at its 5' end, wherein the phosphate group most proximal to the base-pairing moiety (the alpha phosphate) is a methylphosphonate.

11. The method of claim 4, Wherein. the at least one base-pairing moiety comprises at least three phosphate groups at its 5' end, wherein the phosphate group most proximal to the base-pairing moiety (the alpha phosphate) is a boranophosphate.

12. The method of claim 1, wherein the length of time between binding of the nucleotide analog at the active site of the reaction complex and removal of the label moiety from the nascent strand is from about 50 to 250 milliseconds.

13. The method of claim 1, wherein the method is performed under conditions whereby the length of time between two successive detecting steps (d) is from about 0.2 seconds to 1 second.

14. The method of claim 1, wherein the method is performed under conditions whereby the length of time between two successive detecting steps (d) is from about 0.2 to 0.6 seconds.

15. The method of claim 1, wherein the method is performed under conditions whereby the length of time between two successive detecting steps (d) is from about 0.3 to 0.5 seconds.

16. The method of claim 1, wherein repeating steps (c)-(e) to determine the sequence of the target nucleic acid in step (f) comprises continuously monitoring and recording the sequential incorporation of each photo-detectable label in the label moiety of nucleotide analogs being sequentially incorporated into the primer strand.

17. The method of claim 1, wherein n is 1, $R_1$ is

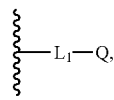

and $R_2$ is $O^-$.

18. The method of of claim 1, wherein $Y_1$ is $S^-$.

19. The method of claim 1, wherein $R_3$ is

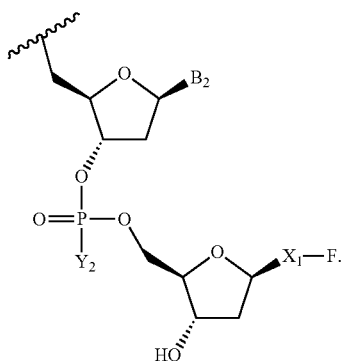

20. The method of claim 1, wherein $Y_3$ is $O^-$.

21. The method of claim 1, wherein the plurality of nucleotide analogs comprises at least four types of nucleotide analogs, each type comprising a unique base-pairing moiety and a unique fluorophore that is distinguishable from the fluorophores of the other types of nucleotide analogs of said plurality.

22. The method of claim 21, wherein the plurality of nucleotide analogs further comprises at least one nucleotide analog having a fluorescence quenching moiety that is removed from the nucleotide analog upon incorporation of the nucleotide analog into the nascent strand.

23. A method of determining a nucleotide base incorporated by a polymerase enzyme or enzyme complex in a nucleic acid polymerization reaction, the method comprising the steps of:

(a) conducting a nucleic acid polymerization reaction that utilizes both 5' to 3' polymerization activity and 3 to 5' exonuclease activity of a polymerase enzyme or enzyme complex, and that results in production of a nascent strand in a template-dependent manner, Wherein said reaction is conducted in the presence of (i) a template nucleic acid comprising a target nucleic acid sequence, (ii) a primer nucleic acid comprising a sequence which is complementary to a region of the template nucleic acid, (iii) a polymerase enzyme or an enzyme complex comprising 5' to 3' polymerization activity and 3' to 5' exonuclease activity, (iv) a plurality of nucleotide analogs, wherein at least one nucleotide analog of said plurality comprises at least one base-pairing moiety, at least one non complementary nucleotide residue, and at least one label moiety, said label moiety comprising a photo-detectable label, wherein the at least one nucleotide analog of said plurality is chosen from compounds having formula I:

Formula I

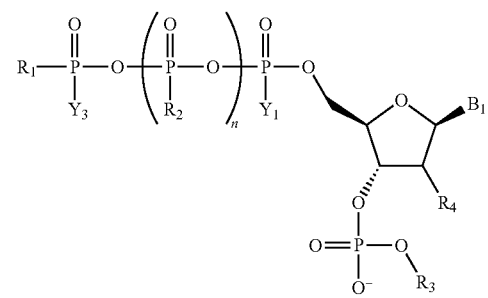

or a pharmaceutically acceptable salt or hydrate thereof, wherein n is 1, 2, 3, 4, 5, 6, 7, 8, or 9;

$R_1$ and each $R_2$ are $O^-$; or $R_1$ is

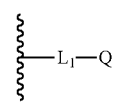

and each $R_2$ is $O^-$; or $R_1$ is $O^-$, one $R_2$ is

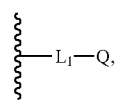

and any remaining $R_2$ is independently $O^-$, $S^-$, $BH_3^-$, or $CH_3$;

$R_3$ is chosen from:

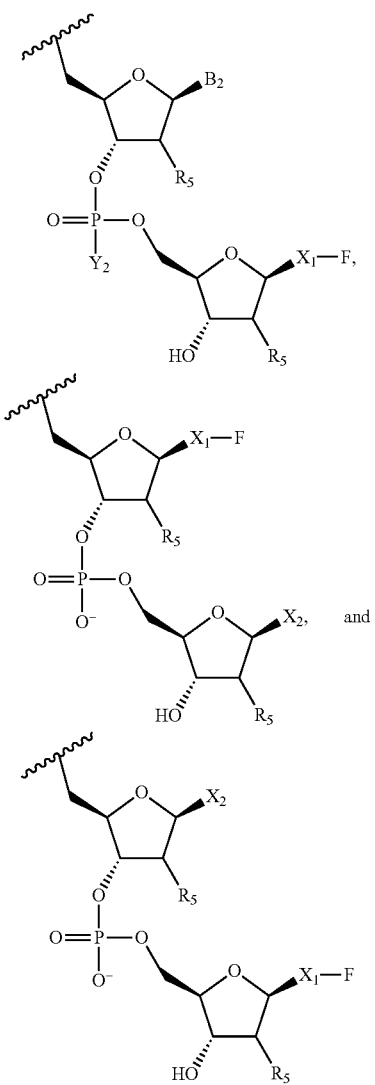

wherein;
- $B_2$ is chosen from adenine, cytosine, guanine, thymine, uracil, hypoxanthine, and 5-methylcytosine;
- $X_1$ is chosen from methylene; $L_2$; a base which does not base pair with any of adenine, cytosine, guanine, thymine, and uracil; and groups comprising $L_2$ and a base which does not base pair with any of adenine, cytosine, guanine, thymine, and uracil, wherein $L_2$ is chosen from alkyl, alkenyl, alkynyl, aryl, heteroaryl, heterocyclyl, ester, amino, and sulfonyl;
- $X_2$ is chosen from H, $CH_3$, and a base which does not base pair with any of adenine, cytosine, guanine, thymine, and uracil;
- each $R_5$ is independently H, OH, fluorine, or $OCH_3$;
- $Y_2$ is chosen from $O^-$, $S^-$, $BH_3^-$, and $CH_3$
- F is a fluorescent dye;
- $R_4$ is H, OH, halogen, alkyl (both substituted and unsubstituted), or alkoxy (both substituted and unsubstituted);
- $Y_1$ and $Y_3$ are each independently chosen from $O^-$, $S^-$, $BH_3^-$, and $CH_3$;
- $L_1$ is chosen from alkyl, alkenyl, alkynyl, aryl, heteroaryl, heterocyclyl, ester, amino, and sulfonyl;
- Q is a fluorescence quenching moiety; and
- B1 is chosen from adenine, cytosine, guanine, thymine, uracil, hypoxanthine, and 5-methylcytosine, wherein the label moiety of an individual nucleotide analog becomes incorporated into the nascent strand and the 3' to 5' exonuclease activity of the enzyme or enzyme complex is allowed to remove the label moiety from the nascent strand; and (b) detecting the photo-detectable label, wherein said label is indicative of the identity of the base or bases present in the nucleotide analog incorporated by the enzyme or enzyme complex into the nascent strand.

24. The method of claim 23, wherein said detecting step is performed during each successive nucleotide incorporation event after the photo-detectable label of the nucleotide analog incorporated in the previous incorporation event is removed via the 3' to 5' exonuclease activity of the enzyme or enzyme complex.

25. The method of claim 1 or 23, wherein the target nucleic acid sequence comprises sequence repeats.

26. The method of claim 1 or 23, wherein the target nucleic acid sequence comprises one or more sequence repeats selected from (A)n, (T)n, (C)n, or (G)n, wherein n is an integer of 3 or greater.

27. The method of claim 1, wherein $R_5$ is H.

28. A method of determining the nucleotide sequence of a target nucleic, acid sequence, comprising the steps of:
(a) providing a reaction complex comprising a template nucleic acid comprising a target nucleic acid sequence, a primer nucleic acid comprising a sequence which is complementary to a. region of the template nucleic acid, and a polymerase enzyme or an enzyme complex, which comprises 5' to 3' polymerization activity and 3' to 5' exonuclease activity;
(b) contacting the reaction complex with a plurality of nucleotide analogs;
(c) allowing the enzyme or enzyme complex to incorporate a nucleotide analog in a template-dependent manner into a nascent strand via 5' to 3' polymerization activity of the enzyme or enzyme complex;
(d) detecting the photo-detectable label moiety of the incorporated nucleotide analog;
(e) allowing the enzyme or enzyme complex to remove the label moiety of the incorporated nucleotide analog from the nascent strand via 3' to 5' exonuclease activity of the enzyme or enzyme complex; and
(f) repeating steps (c)-(e) to determine the sequence of the target nucleic acid sequence, wherein at least one of the nucleotide analogs is chosen from compounds having formula I:

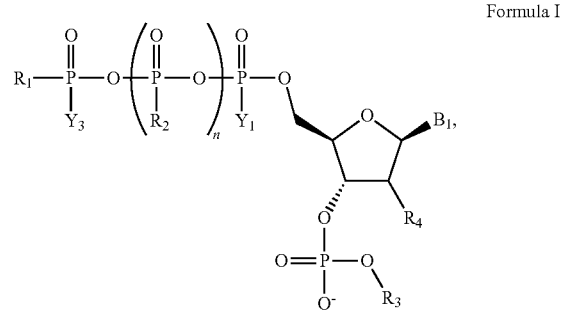

Formula I wherein
 n is 1, 2, 3, 4, 5, 6, 7, 8, or 9;
 $R_1$ and each $R_2$ are $O^-$; or $R_1$ is

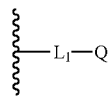

and each $R_2$ is $O^-$; or $R_1$ is $O^-$, one $R_2$ is

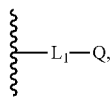

and any remaining $R_2$ is independently $O^-$, $S^-$, $BH_3^-$, or $CH_3$ ;
 $R_3$ is chosen from:

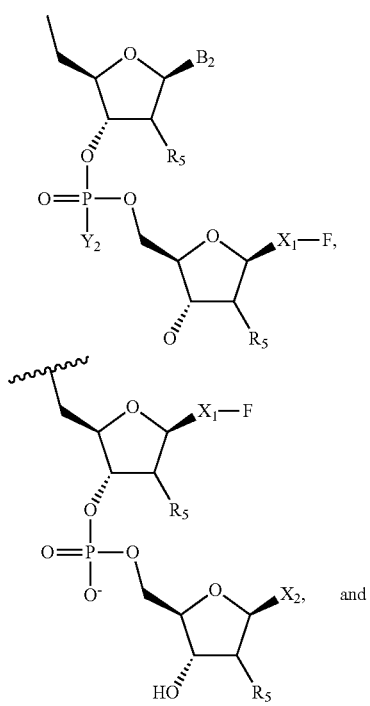

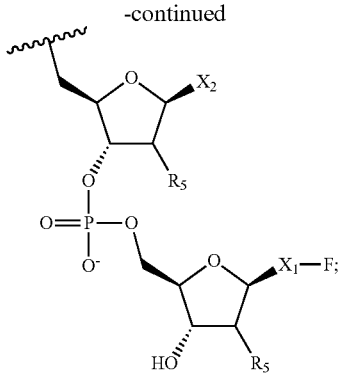

wherein
 B is chosen from adenine, cytosine, guanine, thymine, uracil, hypoxanthine, and 5-methylcytosine;

$X_1$ is chosen from methylene; $L_2$; a base which does not base pair with any of adenine, cytosine, guanine, thymine, and uracil; and group comprising $L_2$ and a base which does not base pair with any of adenine, cytosine, guanine, thymine, and uracil; wherein $L_1$ is chosen from alkyl, alkenyl, alkynyl, aryl, heteroaryl, heterocyclyl, ester, amino, and sulfonyl;

$X_2$ is chosen from H, $CH_3$, and a base which does not base pair with any of adenine, cytosine, guanine, thymine, and uracil;

each $R_5$ is independently H, OH, fluorine, or $OCH_3$; and

Y2 is chosen from $O^-$, $S^-$, $BH_3^-$, and $CH_3$ ; and

F is a fluorescent dye;

$R_4$ is H, OH, halogen, alkyl (both substituted and unsubstituted), or alkoxy (both substituted and unsubstituted);

$Y_1$, and $Y_3$ are each independently chosen from $O^-$, $S^-$, $BH_3^-$, and $CH_3$ ;

$L_1$ is chosen from alkyl, alkenyl, alkynyl, aryl, heteroaryl, heterocyclyl, ester, amino, and sulfonyl;

Q is a fluorescence quenching moiety; and $B_1$ is chosen from adenine, cytosine, guanine, thymine, uracil, hypoxanthine, and 5-methylcytosine.

* * * * *

UNITED STATES PATENT AND TRADEMARK OFFICE
CERTIFICATE OF CORRECTION

PATENT NO. : 9,670,243 B2
APPLICATION NO. : 13/117565
DATED : June 6, 2017
INVENTOR(S) : Chung-Fan Chiou et al.

It is certified that error appears in the above-identified patent and that said Letters Patent is hereby corrected as shown below:

In the Claims

Claim 1, Column 52, Line 17, "Wherein" should read --wherein--.

Claim 11, Column 54, Line 59, "Wherein" should read --wherein--.

Claim 23, Column 56, Line 6, "Wherein" should read --wherein--.

Claim 28, Column 59, Lines 17-32, "$R_3$ is chosen from:

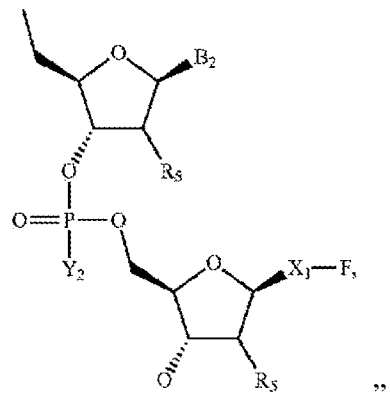

"

Signed and Sealed this
Fifteenth Day of August, 2017

Joseph Matal
*Performing the Functions and Duties of the
Under Secretary of Commerce for Intellectual Property and
Director of the United States Patent and Trademark Office* should read --R₃ is chosen from:
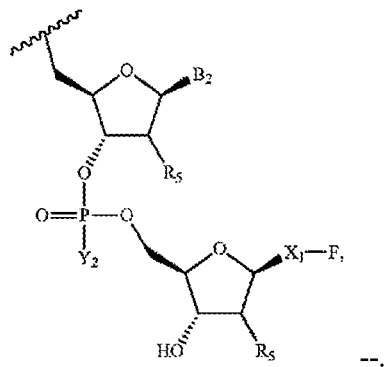
--.
Claim 28, Column 60, Line 25, "wherein $L_1$ is chosen" should read --wherein $L_2$ is chosen--.